United States Patent
Eng et al.

(10) Patent No.: US 9,011,700 B2
(45) Date of Patent: Apr. 21, 2015

(54) SYSTEMS, DEVICES, AND METHODS FOR DIRECTLY ENERGIZING WATER MOLECULE COMPOSITION

(75) Inventors: Hans-Joachim Eng, Seattle, WA (US); Bruce William Adams, West Vancouver (CA)

(73) Assignee: eng3 Corporation, Seattle, WA (US)

( * ) Notice: Subject to any disclaimer, the term of this patent is extended or adjusted under 35 U.S.C. 154(b) by 1123 days.

(21) Appl. No.: 12/324,513

(22) Filed: Nov. 26, 2008

(65) Prior Publication Data

US 2009/0134098 A1    May 28, 2009

Related U.S. Application Data

(60) Provisional application No. 60/990,257, filed on Nov. 26, 2007.

(51) Int. Cl.
| | | |
|---|---|---|
| C02F 1/30 | (2006.01) | |
| C02F 1/32 | (2006.01) | |
| C02F 1/00 | (2006.01) | |
| A61K 8/19 | (2006.01) | |
| A61Q 19/00 | (2006.01) | |

(52) U.S. Cl.
CPC . *C02F 1/005* (2013.01); *A61K 8/19* (2013.01); *A61K 2800/81* (2013.01); *A61Q 19/00* (2013.01); *C02F 1/30* (2013.01)

(58) Field of Classification Search
CPC ..................................... C02F 1/32; C02F 1/30
USPC ............ 210/748.01, 748.1, 205, 149; 422/24, 422/28, 186, 186.3; 204/157.5; 250/436; 261/81; 601/1, 41, 48; 128/203.12, 128/203.18, 204.18, 200.24, 200.262
See application file for complete search history.

(56) References Cited

U.S. PATENT DOCUMENTS

| | | | | |
|---|---|---|---|---|
| 5,778,685 A | * | 7/1998 | Singh et al. | 62/66 |
| 6,555,011 B1 | * | 4/2003 | Tribelsky et al. | 210/748.03 |
| 2004/0005260 A1 | * | 1/2004 | Mulvaney | 422/305 |
| 2004/0022675 A1 | * | 2/2004 | An | 422/29 |
| 2005/0269254 A1 | * | 12/2005 | Roitman | 210/252 |
| 2006/0144690 A1 | * | 7/2006 | Fink et al. | 204/157.5 |
| 2008/0078382 A1 | * | 4/2008 | LeMahieu et al. | 128/200.24 |

FOREIGN PATENT DOCUMENTS

| | | |
|---|---|---|
| CA | 2353499 A1 | 6/2000 |
| JP | 55155794 A | 12/1980 |
| JP | 07108147 A * | 4/1995 |
| JP | 2005-089414 | 4/2005 |
| JP | 2007-51826 A | 3/2007 |
| WO | 00/32520 A1 | 6/2000 |
| WO | 2006/075908 A1 | 7/2006 |

* cited by examiner

*Primary Examiner* — Walter D Griffin
*Assistant Examiner* — Cameron J Allen
(74) *Attorney, Agent, or Firm* — Seed IP Law Group PLLC

(57) ABSTRACT

Systems, devices, and methods for generating energized water molecules and administering same to a human or other biological subject. The system includes a humidifying apparatus, and excitation apparatus, and a control system. The system may further include a fluid management system to assist in the delivery of energized water molecules.

17 Claims, 8 Drawing Sheets

SYSTEMS, DEVICES, AND METHODS FOR DIRECTLY ENERGIZING WATER MOLECULE COMPOSITION

CROSS-REFERENCE AND RELATED APPLICATIONS

This application claims the benefit under 35 U.S.C. §119 (e) of U.S. Provisional Patent Application No. 60/990,257, filed Nov. 26, 2007, which application is incorporated herein by reference in its entirety.

BACKGROUND

1. Technical Field

This disclosure generally relates to systems, devices, and methods for energizing water molecule compositions and for delivering energized water molecules to a biological subject or bulk water. This disclosure is also generally related to systems, devices, and methods for modifying hydrogen bonding behavior of water molecules and subsequently affecting biological processes in biomolecules, particularly proteins.

2. Description of the Related Art

Hydrogen bonding of water molecules provides this unique solvent with properties essential to many physical, chemical, and biological processes. Hydrogen bond, the faint force between hydrogen and the more electronegative oxygen, is known to have vibrational phases that may be excited by numerous forms of energy transfer. The vibrational excitation of hydrogen bonds in water is at the basis of fundamental processes such as the ability of molecules to dissolve in water, the motion of protons and other charges in water, and biological processes such as protein folding, proton transfer across the surface of proteins, and the like.

WO00/32520 describes using excited singlet oxygen to activate atomized water drops. As a result of the activation process, the structure and hydrogen bonding behaviors of the water have changed. The "activated water" can be used in a multitude of applications such as medicine, agriculture, printing, etc. This process of activating the water requires an oxygen source to produce the singlet oxygen; however, there is no or little control of the energy transferred from the singlet oxygen to the water. In addition, the production of singlet oxygen involves complex photosensitization in the presence of catalysts, which pose environmental concerns.

The present disclosure is directed to overcoming one or more of the shortcomings set forth above, and providing further related advantages.

BRIEF SUMMARY

Generally speaking, it is described herein a system for directly activating a water molecule composition to produce excited water and methods of making and using same.

A system for producing energized water may be summarized as including a humidifying apparatus for generating a water molecule composition in a carrier gas, the water molecule composition being a water aerosol composition, water vapor, or a combination thereof, wherein the water aerosol composition includes water droplets suspended in the carrier gas, the water droplets being of micron-size, nano-size or a combination thereof; an excitation apparatus for directly irradiating the water molecule composition to provide energized water; and a control system operable to direct an electromagnetic radiation to irradiate the water molecule composition.

The humidifying apparatus may convert pure water or an aqueous composition to the water aerosol composition. The aqueous composition may comprise salts, minerals, vitamins, or one or more biologically active agents. The humidifying apparatus may convert pure water or an aqueous composition to water vapor. The carrier gas may be air, $O_2$, Ar, $N_2$. The humidifying apparatus may further comprise a temperature control element. The excitation apparatus may comprise one or more energy-emitting elements that provide electromagnetic radiation in a range of 240 nm to 7000 nm. The electromagnetic radiation may be 520 nm, 640 nm, 1200 nm, 2900 nm, or a combination thereof. The one or more energy-emitting elements may be a laser, a laser diode, a light emitting diode (LED), an arc flashlamp, or a continuous wave bulb. The energy-emitting elements may provide two or more irradiation wavelengths. The energized water may comprise excited state clathrate structures. The system may further comprise a fluid management system which may be communicatively coupled to the excitation apparatus and operable to direct a flow of the water molecule composition.

A method of forming an energized water composition may be summarized as including generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; and directing an electromagnetic radiation to irradiate the water molecule composition.

Directing an electromagnetic radiation to irradiate the water molecule composition may include controlling, selecting, or combining one or more electromagnetic energy outputs created by an energy-emitting element. Irradiating the water molecule composition may comprise directly irradiating the water molecule composition at one or more peak emission wavelengths in an optical range of the electromagnetic spectrum including an infrared, a visible, or an ultraviolet portion of the electromagnetic spectrum, or combinations thereof. Directing an electromagnetic radiation to irradiate the water molecule composition may comprise directly irradiating the water molecule composition at one or more peak emission wavelengths in a non-optical range of the electromagnetic spectrum including a thermal, a microwave, a nuclear magnetic resonance, or a combination thereof. Directing an electromagnetic radiation to irradiate the water molecule composition may comprise directly irradiating the water molecule composition at a wavelength selected from 520 nm, 640 nm, 1200 nm and 2900 nm. Directing an electromagnetic radiation to irradiate the water molecule composition may comprise directly irradiating the water molecule composition at two or more wavelengths. Irradiating the water molecule composition may comprise directly irradiating the water molecule composition at two wavelengths of 640 nm and 1200 nm or at three wavelengths of 520 nm, 640 nm and 1200 nm. Directing an electromagnetic radiation to irradiate the water molecule composition may comprise directly irradiating the water molecule composition for about 1 nanosecond to 60 seconds. Directing an electromagnetic radiation to irradiate the water molecule composition may include directly irradiating the water molecule composition in an intermittent or pulsing pattern. Directing an electromagnetic radiation to irradiate the water molecule composition may generate water clathrate structures.

A method for modulating protein functions in a biological subject may be summarized as including generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and contacting the energized water with the biological subject.

Directing an electromagnetic radiation to irradiate the water molecule composition may include providing a sufficient amount of electromagnetic energy having one or more wavelengths in the range of about 10 nm to about $1 \times 10^6$ nm to the water molecule composition that results in the formation of one or more clathrate structures or clustered structures within the water droplets. Directing an electromagnetic radiation to irradiate the water molecule composition may include providing a sufficient amount of electromagnetic energy having one or more wavelengths in the range of about 10 nm to about $1 \times 10^6$ nm to the water molecule composition that causes a pH change therein. Directing an electromagnetic radiation to irradiate the water molecule composition may include providing a sufficient amount of electromagnetic energy having one or more wavelengths in the range of about 10 nm to about $1 \times 10^6$ nm to the water molecule composition that causes a redox potential change therein. Directing an electromagnetic radiation to irradiate the water molecule composition may include irradiating the water molecule composition at a wavelength selected from 520 nm, 640 nm, 1200 nm and 2900 nm.

A method of affecting a physiologic process of a biological subject associated with aquaporin-mediated water transport may be summarized as including generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and delivering the energized water to a region of the biological subject associated with aquaporins.

A method for affecting hydrogen-bonding process may be summarized as including generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and contacting the energized water with molecules that participate in hydrogen bonding.

A method for reducing oxidative stress may be summarized as including generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and delivering the energized water to a biological subject, whereby the hydronium ions at the excited states of the water are combined with reactive oxygen species to render the reactive oxygen species less reactive or inactive.

A method of modifying bulk water may be summarized as including generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and contacting the energized water with bulk water.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

DETAILED DESCRIPTION

Figure 1:
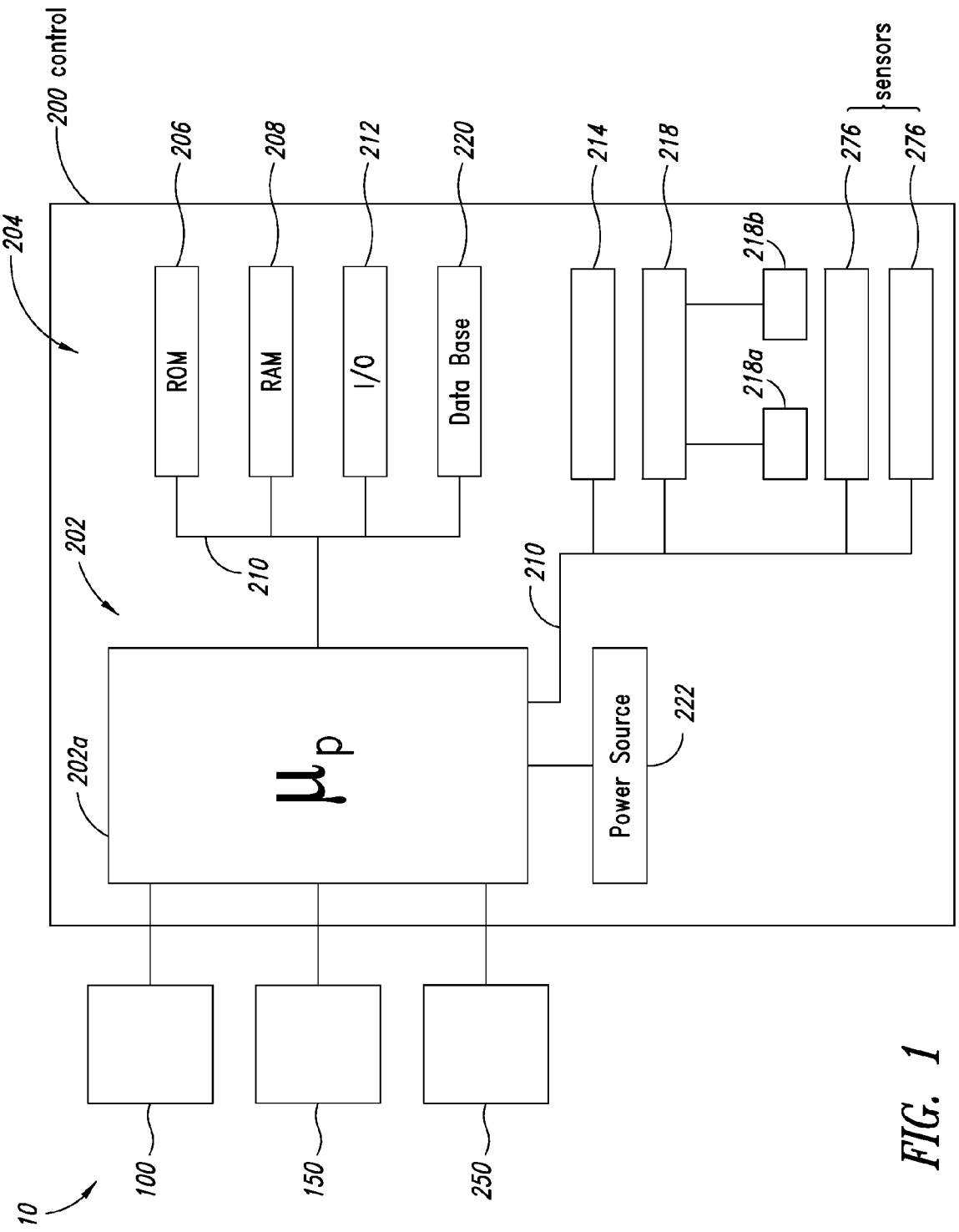
FIG. 1 is a schematic diagram of a system for delivering an excited water molecule composition to a biological subject according to one illustrated embodiment.

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with electrically powered devices including but not limited to voltage and/or current regulators have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment," or "in some embodiments" means that a particular referent feature, structure, or characteristic described in connection with the embodiment is included in at least one embodiment. Thus, the appearance of the phrases "in one embodiment," or "in an embodiment," or "in another embodiment," or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to a system for delivering an excited-water molecule device including an "excitation chamber" includes a single excitation chamber, or two or more excitation chambers. It should also be noted that the term "or" is generally employed in its sense including "and/or" unless the content clearly dictates otherwise.

In general, it is described herein systems and processes for directly activating water molecule composition to produce excited or energized water molecules, which in turn can be delivered to bulk water or biological system. The activated water is believed to modify the behaviors of hydrogen bonds in biomolecules (e.g., proteins), redox-sensitive substances, bulk water, water-mediated biological processes or protein-mediated biological processes.

"Hydrogen bond" refers to a non-covalent attractive force between a hydrogen attached to an electronegative atom of one molecule and an electronegative atom of a different molecule. When hydrogen bonding occurs between two molecules, it is also referred to as "intermolecular hydrogen bonding." Typically, the hydrogen has a partial positive charge due to the electronegative atom it is attached to (e.g., oxygen in a water molecule). The positively charged hydrogen is thus attracted to an electronegative atom (e.g., oxygen, nitrogen, or fluorine) of another molecule (e.g., oxygen in another water molecule). Intramolecular hydrogen bonding occurs within a single molecule, in which a partially positively charged hydrogen atom attached to an electronegative atom in one portion of the single molecule can be attracted to another electronegative atom of another portion of the same molecule.

An important feature of the hydrogen bond is that it is directional, the direction being that of the shorter O—H covalent bond for water molecules (the hydrogen atom of the O—H bond is being donated to the oxygen atom of another water molecule). As a result, a given molecule is restricted in the number of hydrogen bonds it can form with neighboring molecules. For water molecules, the number is typically four. Formation of multiple hydrogen bonds between water molecules gives rise to a hydrogen bond network.

The hydrogen bond network is typically dynamic and the behavior and energy fluctuations therein are impacted by factors such as orientation and vibrational frequencies of the water molecules. By changing its orientation with respect to its surroundings, a water molecule may stretch or break one or more hydrogen bonds. Additionally, the O—H stretch vibrational frequencies of the water molecules strongly correlate with the strength of the hydrogen bonds.

Certain energy transfer to water molecules can excite or energize the O—H stretch vibrational modes of the hydrogen bonds. There exists various excited states of $H_2O$ and the diffusion, relaxation and reorientation from the excited (or energized) states of the O—H stretch vibration will lead to a change of the hydrogen bond dynamics of liquid water.

As used herein, the terms "excite", "activate", "energize", "irradiate" or "stimulate" interchangeably refer to a process that adds a discrete amount of energy ("excitation energy") to a system such as atom(s) and molecule(s), which results in a transition of the system from a baseline energy state ("ground state") to one of higher energy state ("excited state"). For example, excited electronic or vibrational states usually occur following the absorption of radiation of certain frequency (e.g., that corresponds to the energy differentials between the ground state and the excited state). The excited state is typically short-lived and can return to the ground state through processes such as radiative emission (fluorescence), thermal emission (heat) and by reaction.

The vibrational dynamics of water in the proximity of a surface (i.e., interfacial water) demonstrate different behaviors depending on the phase states of the water, i.e., whether the water is in liquid or gaseous phases. For liquid water, the vibrational dynamic also differs depending on whether the liquid water is bulk or confined.

In bulk liquid water, there exists a high concentration of near resonant O—H oscillators. As a result, these oscillators show a dipolar (Forster) energy-transfer process that is completely independent of the structural (hydrogen bond) dynamics of the liquid.

Liquid water in a confined geometry, on the other hand, shows significant difference in its structural characteristics from water in the bulk phase. For example, energy transfer of confined water involves a mechanism that is essentially different from the mechanism of resonant energy transfer in bulk liquid water. For confined water molecules, energy transfer occurs only after the two O—H oscillators are shifted into resonance. Thus, the energy flow within the molecule is governed completely by the rate at which hydrogen bonds are being broken and reformed, which slows down the energy transfer by a factor of about 20 in comparison with bulk water.

As used herein, "confined water" refers to liquid water confined to a particular environment, such as hydrophilic and hydrophobic surfaces, surfaces of biomolecules, porous media, air, etc. In certain embodiments, confined water is spherically confined due to surface tension at the water-air interface. An example of spherically confined water is water aerosol, which refers to fine droplets of water suspended in gas (e.g., air). In various embodiments, the droplets are micron-size (no more than in 1 cm in diameters), nano-sized (no more than 1 μm in diameters), or a combination thereof. In other embodiments, confined water includes water molecules surrounding biomolecules. These water molecules are typically involved in reactions and hydration of biomolecules and are located in highly confined geometries.

At excited states, confined water will form hydrogen bond clusters which will retain the molecular energy in the vibrational state of the bonds. Clathrate structures, in which small nonpolar molecules (typically gases) are trapped inside "cages" or "clusters" of hydrogen bond network of the water molecules, are largest and strongest at the point of their creation, and will continue to collapse to a 'ground state' as they interact with their environment. It is believed that confined water (such as a water aerosol) at excited states can adopt clathrate structures. Such structure is also referred to as "clustered structure" or "water clusters".

Gaseous water, i.e., water vapor, is also characterized with dynamic and energized hydrogen bond network at the excited state.

For purpose of this disclosure, "water molecule composition" refers to water aerosol, water vapor or a combination thereof. At the excited states, water molecule composition (regardless of its structures) is also referred to as "energized water."

A. System for Energizing Water

Because the energy transfer of confined water is governed by the rate of breaking and reforming of hydrogen bonds, confined water at excited state adopts certain dynamic structures, which are characterized with changes of the hydrogen bond network at the surface interface between water and air. These structures, including clathrate or cluster structures, are believed to be capable of further modifying the hydrogen bonding behaviors of the surrounding molecules (including biomolecules) of the confined water. Similar to the water aerosol, water vapor at the excited state exhibits similar behaviors. Thus, the energized water molecules in turn are capable of altering the physical, chemical or biological activities of the surrounding molecules.

Thus, one embodiment provides a system for producing energized water, the system comprising: a humidifying apparatus for generating a water molecule composition, the water molecule composition being a water aerosol composition, water vapor or a combination thereof, an excitation apparatus for directly irradiating the water molecule composition, and a control system.

FIG. 1 shows an exemplary system 10 for delivering an excited or energized water molecule composition to a biological subject. The system 10 includes an excitation apparatus 100, a humidifying apparatus 150, and a control system 200. The system 10 may further include fluid management system 250 and one or more sensors 276.

Figure 2:
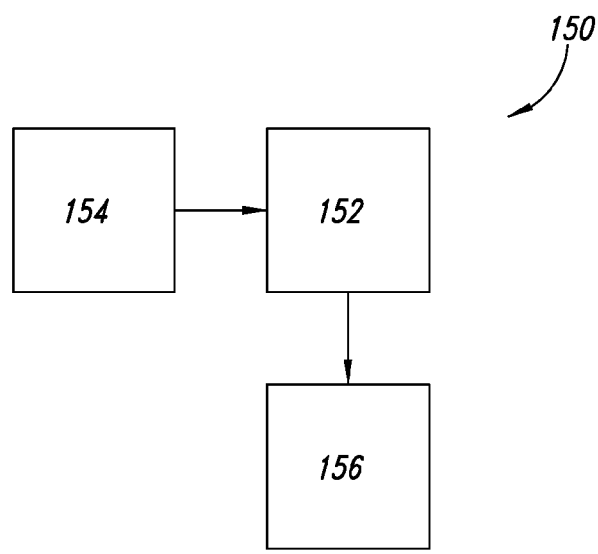
FIG. 2 is a schematic diagram of a humidifying apparatus.

Humidifying Apparatus:

The humidifying apparatus 150 converts or vaporizes bulk water into a water molecule composition, which can be a water aerosol composition, i.e., fine water droplets suspended in a carrier gas, or water vapor, which is a gaseous mixture of water vapor and the carrier gas, or a combination thereof. The humidifying apparatus 150 typically comprises a humidifying chamber 152, a carrier gas source 154 and an optional temperature-control element 156 (FIG. 2)

The humidifying chamber may utilize pure water, aqueous compositions, or other fluids, collectively referred to as "fluid." The resulting water aerosol or water vapor can be further characterized by certain pH values and redox potentials, depending on the excitation energy, the nature of the additional components in the aqueous composition, and the like. For example, the aqueous composition may further comprise salts, minerals, vitamins, or one or more biologically active agents. "Biologically active agent" generally refers to a compound that elicits a biological response from any biological subject. Examples of active agents include, without limitation, therapeutic agents, pharmaceuticals (e.g., a drug, a therapeutic compound, pharmaceutical salts, and the like) non-pharmaceuticals (e.g., a cosmetic substance, and the like), neutraceuticals, antioxidants, phytochemicals, homeopathic agents, anesthetics and the like.

In some embodiments, the fluid could be delivered by venturi, or gravity induced flow. In some embodiments, the water may not have to be suspended in a carrier gas for delivery to the excitation apparatus 100. Such water-enriched fluid in the gas stream may aid in increasing the relative humidity.

A carrier gas source provides a constant supply of carrier gas mixture to system 10, such as required by the specific application. The carrier gas source typically includes a cylinder containing a carrier gas, an ambient air intake, and the like. Examples of a carrier gas include, for example, air, $O_2$, Ar, $N_2$, and the like. In some embodiments, oxygen ($O_2$) may be used and mixed with ambient air. Other gases may be used that either affect the way clathrate structures form in the excitation apparatus or affect the way that the biological subject will be exposed to the treatment molecules that exit from the device. For instance, $O_2$ may influence wound healing. In some embodiment, for a non-inhalation device, or a device that will not interact with a biological subject, argon or nitrogen alone might be used as a carrier gas. It is also possible that the gas mixture could be further mixed with other gases and/or fluids, before or after entering the excitation apparatus 100. In some embodiments, the gas mixture could be infused with other treatment molecules such as pharmaceuticals, neutraceuticals, homeopathic medicines, and the like, that would work in conjunction with the excited state molecules from the excitation apparatus 100.

Optionally, a temperature control element is present to provide direct control of the heating and cooling of the resulting water molecule composition. Elevated temperatures, for example, may increase the relative humidity. i.e., the amount of the water vapor in the water molecule composition. Some embodiments may operate at a temperature ranging from about 20° C. to about 40° C., where the fluid is water and relative humidity is between about 50% to about 100%. Higher operating temperatures may allow for greater water vapor content (e.g., relative humidity) in the water molecule composition. Lower operating temperatures may allow water vapor to condense into water aerosol.

The water aerosol composition typically comprises water droplets of less than 1 mm in diameters. The sizes of the water droplets can be determined by known technique in the art, such as optical (with digital camera or film) or laser diffraction. In various embodiments, the water droplets are micronsized, nano-sized or a mixture of both. In certain embodiments, the water droplets have diameters smaller than 500 µm, 250 µm, 100 µm, 50 µm, 500 nm, 250 nm, 100 nm or 50 nm. Monodispersity in droplet sizes is possible but not required. In certain embodiments, the water droplets have diameters ranging between 50 nm to 750 µm, 100 nm to 500 nm, 250 nm to 750 nm, 500 nm to 1 µm, 500 nm to 100 µm, 1 µm to 750 µm, 100 µm to 500 µm, 100 µm to 250 µm and the like. The density of the droplets in the water aerosol composition (i.e., number of droplets per unit volume) can be adjusted by controlling factors such as the fluid to carrier gas ratio, their respective flux rates and flux pattern and the temperature according to known techniques in the art. The density can be held at constant or could vary in an intermittent pattern.

After exiting the humidifying apparatus, the water molecule composition enters into the excitation apparatus 100 in a steady stream (i.e., a flow of air stream that transports the water droplets or the water vapor) or in a desired flux pattern.

Excitation Apparatus

In the excitation apparatus, the water molecule composition generated in the humidifying apparatus is directly stimulated to energize the hydrogen bonds. It is desired that the energized water molecules will form clathrate or clustered structures or other high-energy structures. These clusters will ideally form within the micron-sized or nano-sized water droplets.

Referring to FIG. 1, the excitation apparatus 100 directly irradiates the water molecule composition generated by the humidifying apparatus 150 to provide energized water of, for example, clathrate structures. Unlike any of the prior art devices, the excitation apparatus described herein comprises an active energy source that can be controlled by the control system. 200. Thus, the amount (e.g., wavelength), intermittency, intensity and duration of the energy input may be controlled with precision. Additionally, any one or a combination of the above parameters can be dynamically controlled to meet the needs of diverse end-uses of the energized water.

Figure 3:
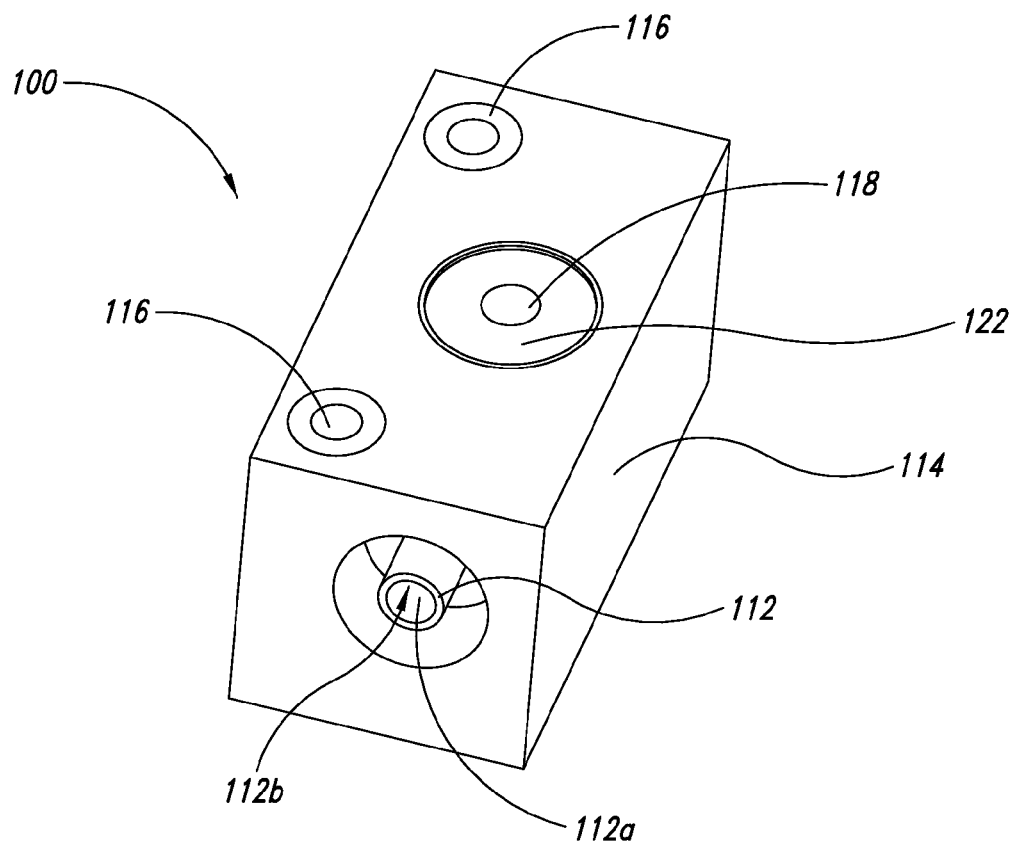
FIG. 3 is an isometric view of an excitation chamber assembly for a system for delivering an excited-water molecule composition to a biological subject according to one illustrated embodiment.

FIG. 3 shows an excitation apparatus 100 for the system 10 according to one illustrated embodiment. In some embodiments, the excitation apparatus 100 includes a housing 114, an excitation chamber 112 having an interior surface 112a and a passageway 112b define by the interior surface 112, and one or more energy-emitting elements 118 in optical communication with the passageway 112b of the excitation chamber 112. In some embodiments, the excitation chamber 112 is carried by or forms part of the housing 114. In some embodiments, the excitation apparatus 100 is operable to optically excite the water molecule composition. In some embodiments, the excitation apparatus 100 includes a housing 114 and one or more fluid conduits having interior surfaces defining one or more passageways for directing the flow of the water molecule composition. In some embodiments the interior surfaces may include one or more energy-emitting elements 118 in optical communication with the passageways and operable to provide optical energy to the water molecule compositions flowing within the passageways.

The energy-emitting element 118 provides electromagnetic energy (radiation) to energize the water molecule composition. Water has multiple absorption peaks throughout the electromagnetic spectrum. An important factor in selecting the energy-emitting element is to identify a peak absorption wavelength that corresponds effectively with the formation of energy-conserving clusters and clathrate structures. Thus, in some embodiments, the one or more energy-emitting elements 118 are capable of emitting one or more different optical energies, or a broadband of optical energies, to cause the formation of desired structures in the disclosed systems, composition, or methods. For example, the different optical energies can have one or more different peak emission wavelengths that result in the formation of one or more clathrate structures or clustered structures within micro-size water clusters and/or nano-size water clusters of any of the disclosed compositions.

Typically, the one or more energy-emitting elements 118 are operable to emit optical energy having one or more peak emission wavelengths in the optical portion of the electromagnetic spectrum, including infrared (IR, near IR, and far IR), visible (VIS) or ultraviolet (UV) range, or combinations thereof. In other embodiments, one or more energy-emitting elements 118 are operable to emit non-optical including thermal, microwave, nuclear magnetic resonance, or a combination thereof. In more specific embodiments, the one or more energy-emitting elements 118 emit in the IR range of about 750 nm to about $1\times10^6$ nm, in particular, of about 750 nm to $1\times10^5$ nm; the VIS range of about 400 nm to about 750 nm, or UV range of about 10 nm to about 400 nm, or combinations thereof. For example, in some embodiments, the one or more energy-emitting elements 118 are operable to emit optical energy having a peak emission wavelength of between about 240 nm to 7000 nm, or between 240 nm to about 3000 nm, or between about 240 nm to about 1000 nm, or between about 500 nm to about 1000 nm, or between about 500 nm to about 1200 nm, or between about 600 nm to about 1500 nm, or between about 500 nm to about 2900 nm, or between about 1000 nm to about 2900 nm, and the like. Preferred peak emissions include, but are not limited to 520 nm, 640 nm, 1200 nm or 2900 nm. It is noted that the optical excitation at 1200 nm and 2900 nm corresponds to OH absorption.

In some embodiments, the one or more energy-emitting elements 118 include at least one of a laser, a laser diode, a light emitting diode (LED), an arc flashlamp, a continuous wave bulb, and the like.

In certain specific embodiments, the energy-emitting element 118 is an optical emitter such as an LED. LEDs, which include organic light-emitting diodes (OLEDs), are preferred optical emitters due to their high intensity and brightness, low current, diverse wavelengths, compact dimensions and the like. The "color" and/or peak emission wavelength spectrum of the emitted light generally depends on the composition and/or condition of the semiconductive material used, and may include peak emission wavelengths in the infrared, visible, near-ultraviolet, and ultraviolet spectrum. For example, red LEDs have a peak emission ranging from about 625 nm to about 660 nm. Examples of LEDs colors include amber, blue, red, green, white, yellow, orange-red, ultraviolet, infrared, and the like. Further examples of LEDs include bi-color, tri-color, and the like. Emission wavelength may also depend on the electrical current delivered to the LEDs.

Table 1 shows a number of wavelengths suitable for exciting the water molecule composition. All of the wavelengths (in nm) in Table 1 can be generated by LEDs that are currently commercially available.

TABLE 1

| LED WAVELENGTH (NM) | | | | | |
|---|---|---|---|---|---|
| 375 | 490 | 645 | 810 | 1300 | 2900 |
| 385 | 505 | 660 | 830 | 1350 | 3100 |
| 395 | 525 | 670 | 850 | 1450 | 3400 |
| 405 | 545 | 680 | 870 | 1550 | 3600 |
| 413 | 565 | 690 | 880 | 1650 | 3800 |
| 415 | 570 | 700 | 890 | 1755 | 4200 |
| 418 | 590 | 720 | 910 | 1850 | 4300 |
| 420 | 600 | 735 | 940 | 1950 | 4500 |
| 422 | 610 | 750 | 970 | 2050 | 4600 |
| 430 | 625 | 760 | 1050 | 2150 | 5000 |
| 450 | 630 | 770 | 1070 | 2250 | 5500 |
| 470 | 635 | 780 | 1200 | 2350 | 7000 |

Additional exemplary wavelengths include the following ranges: 400-600 nm; 550-750 nm; 700-900 nm; 850-1050 nm; 1000-1200 nm; 1150-1350 nm; 1300-1500 nm; 1450-1650 nm; 1600-1800 nm; 1750-1950 nm; 1900-2100 nm; 2050-2250 nm; 2200-2400 nm; 2350-2550 nm; 2500-2700 nm; 2650-2850 nm; 2800-3000 nm; 2950-3150 nm; 3100-3300 nm; 3250-3450 nm; 3400-3600 nm; 3550-3750 nm; 3700-3900 nm; 3850-4050 nm; 4000-4200 nm; 4150-4350 nm; 4300-4500 nm; 4450-4650 nm; 4600-4800 nm; 4750-4950 nm; and 4900-5100 nm.

The use of an LED also allows for small size and positioning of the device where the optical system in its entirety is small enough that it will fit as close to the point of use as possible, for instance in front of the persons nose or mouth much in the same way that light weight microphones are positioned for telephone headsets, with a mounting harness over the head and an adjustable extension to fit in front of the face.

A single energy-emitting element 118 can be adapted to emit any number of peak emission wavelengths (e.g., a single peak emission wavelengths, a range of peak emission wavelengths, or a plurality of discrete peak emission wavelengths) that correspond to the formation of desired excited state structures, e.g., clathrate structures.

In other embodiments, more than one energy-emitting elements are present. These plurality of energy-emitting elements can be separately controlled and emit a combination of discrete wavelengths to generate diverse structures of the excited state water. Any two or more wavelengths discussed herein in connection with a single energy emitting element can be combined.

In certain more specific embodiments, the plurality of energy-emitting elements can be a plurality of two-dimensional LED arrays or at least one three-dimensional LED array. The array of LEDs may be mounted using, for example, a flip-chip arrangement. A flip-chip is one type of integrated circuit (IC) chip mounting arrangement that does not require wire bonding between chips. In some embodiments, instead of wire bonding, solder beads or other elements can be positioned or deposited on chip pads such that when the chip is mounted, and electrical connections are established between conductive traces carried by the system 10. Any two or more wavelengths discussed herein in connection with a single LED (for example, those described in Table 1) can be combined. Exemplary combinations include 640 nm and 1200 nm, or 520 nm and 640 nm and 1200 nm.

In other embodiments, the one or more energy-emitting elements 118 may take the form of a broad band light source with a spectral output from the UV through IR spectral range. In such cases, selective optical filters can be used to control the wavelength band that is incident into the excitation chamber 112. For example, broad band light sources, in combination with optical filters in the red or NIR region, could be used as broadband excitation sources.

In certain embodiments, the one or more energy-emitting elements can be further adapted such that the duration of irradiation, the pulsing or intermittent patterns of irradiation and the intensity of irradiation can be tuned. For example, typical irradiation duration is anywhere between about 1 nanosecond (ns) to about 60 second (s). The pulsing or intermittent patterns can be static or any configuration of patterns and frequencies within the duration of irradiation. The intensity of irradiation, including luminous intensity (perceived power per unit solid angle) of the irradiation of a specific wavelength could have the same or different value than the values for the other wavelengths. Likewise, luminous flux (perceived power emitted in all directions) of a specific wavelength could have the same or different value than the values for the other wavelengths.

In another embodiment, frequency modulation of the excitation source is used to enhance the anisotropy. This may depend upon the speed at which the nano-droplets pass through the energizing field and may further stimulate the OH bond rotations, librations and bending.

In some embodiments, the one or more energy-emitting elements 118 may be located anywhere along a fluid conduit for directing the flow any of the disclosed composition. In some embodiments, the one or more energy-emitting elements 118 may be located anywhere along a fluid conduit for directing any of the disclosed composition. In such embodiment, the excitation chamber 112 of excitation apparatus 100 may be optionally present.

In some embodiments, the LEDs can be "potted" in a clear flexible medium surrounding a short length of an optical fiber.

In some embodiments, the one or more energy-emitting elements 118 may be thermodynamically coupled to independent heat sink elements to allow for ease of assembly and increased heat dissipation.

In some embodiments, the surfaces of the housing 114 may include a coating or optical focusing surfaces to direct energy form the one or more energy-emitting elements 118 towards and through the excitation chamber 112.

In some embodiments, a temperature sensor may be embedded proximate to the one or more energy-emitting elements 118 or in any of the heat sink elements.

In some embodiments, the excitation chamber 112 is substantially optically transparent. The substantially optically transparent excitation chamber may comprise a light-transmitting material. Among the light-transmitting materials examples include infrared window materials such as, for example, AgBr, AgCl, $Al_2O_3$ (Sapphire), AMTIR (GeAsSe Glass), $BaF_2$, $CaF_2$, CdTe, Chalcogenide (AsSeTe glass), CsI, Diamond, GaAs, Ge, ITRAN materials (e.g., IRTRAN-3, IRTRAN-4, IRTRAN-5, and IRTRAN-6 by Eastman Kodak Company), KBr, Thallium Bromide-Iodide (e.g., KRS-5 and KRS-6), LiF, $MgF_2$, NaCl, Polyethylene (high density), Pyrex, Si, $SiO_2$ (quartz), ZnS (CLEARTRAN), ZnSe, and the like.

Further examples of light-transmitting materials include acetal copolymers, acrylic, glass, quartz, thermoplastic polymers, thermoset polymers, acrylonitrile butadaine styrene polymers, cellulosic, epoxy, ethylene butyl acrylate, ethylene tetrafluoroethylene, ethylene vinyl alcohol, fluorinated ethylene propylene, furan, nylon, phenolic, poly[2,2,4-trifluoro-5-trifluoromethoxy-1,3-dioxole-co-tetrafluoroethylene], poly [2,2-b]strifluoromethyl-4,5-difluoro-1,3-dioxole-co-tetrafluoroethylene], poly[2,3-(perfluoroalkenyl) perfluorotetrahydrofuran], polyacrylonitrile butadiene styrene, polybenzimidazole, polycarbonate, polyester, polyetheretherketone, polyetherimide, polyethersulfone, polyethylene, polyimide, polymethyl methacrylate, polynorbornene, polyperfluoroalkoxyethylene, polystyrene, polysulfone, polyurethane, polyvinyl chloride, polyvinylidene fluoride, such as diallyl phthalate, thermoplastic elastomer, thermoset polyester, transparent polymers, or vinyl ester, or combinations thereof. In some embodiments, the substantially optically transparent excitation chamber 112 is a quartz structure.

In some embodiments, the excitation chamber 112 comprises a quartz conduit (e.g., 40 mm×3 mm), a pulsed 250 µW infrared emission diode having a peak emission wavelength of 2.9 µm, a heat sink element, a cooling fan or TEC, and a thermo-sensor. In use, the excitation chamber 112 accepts the water molecule composition. The droplets and/or vapor flow through the quartz conduit into the optical path of the excitation energy from the diode. The excitation chamber 112 conduit is quartz so as to allow, for example, infrared energy to pass, but to minimize the effects of electrostatic fields. Other materials may be used such as, for example, ceramic materials. The conduit structure may include a wider chamber in front of the optical axis to create an expanding waveform of gas and droplets as they transit the optical excitation path. This may help to create clathrate structures.

Figure 4:
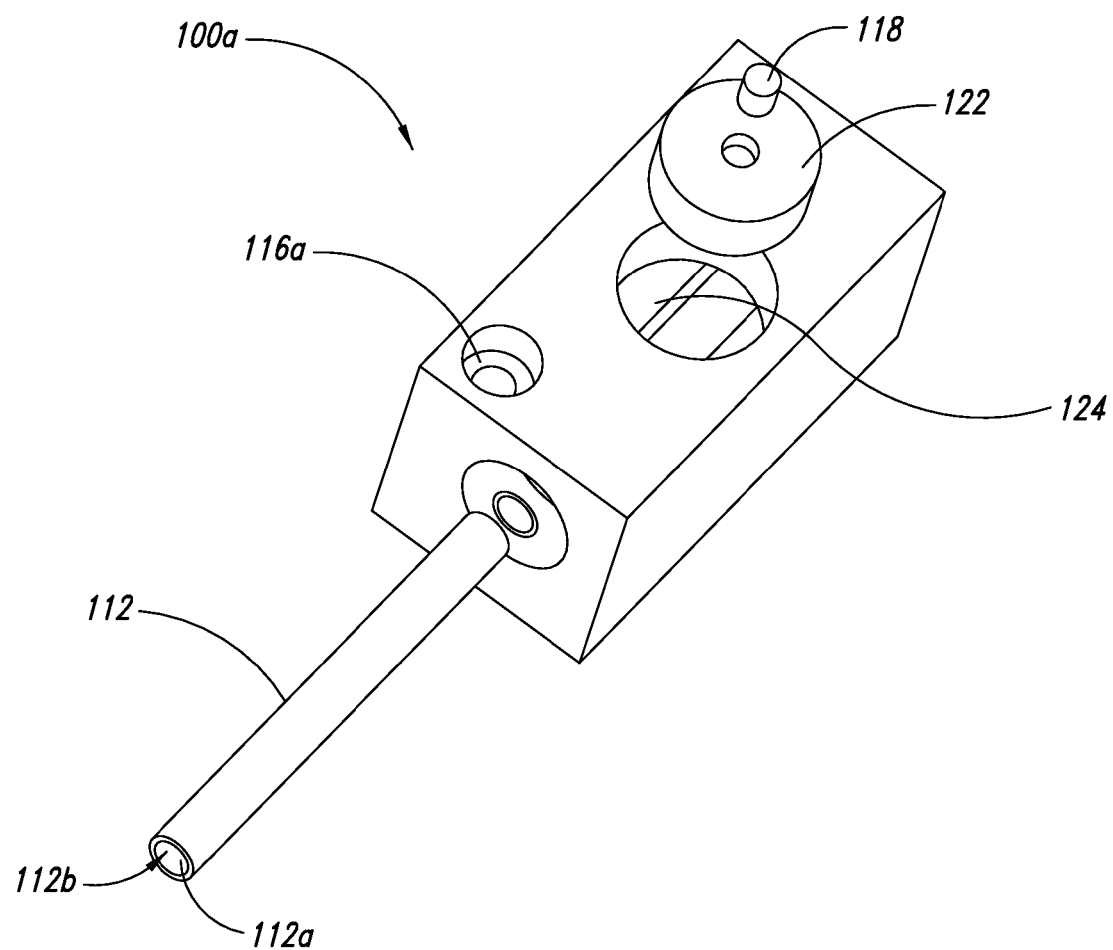
FIG. 4 is an exploded view of the assembly of FIG. 3 according to one illustrated embodiment.
Figure 5:
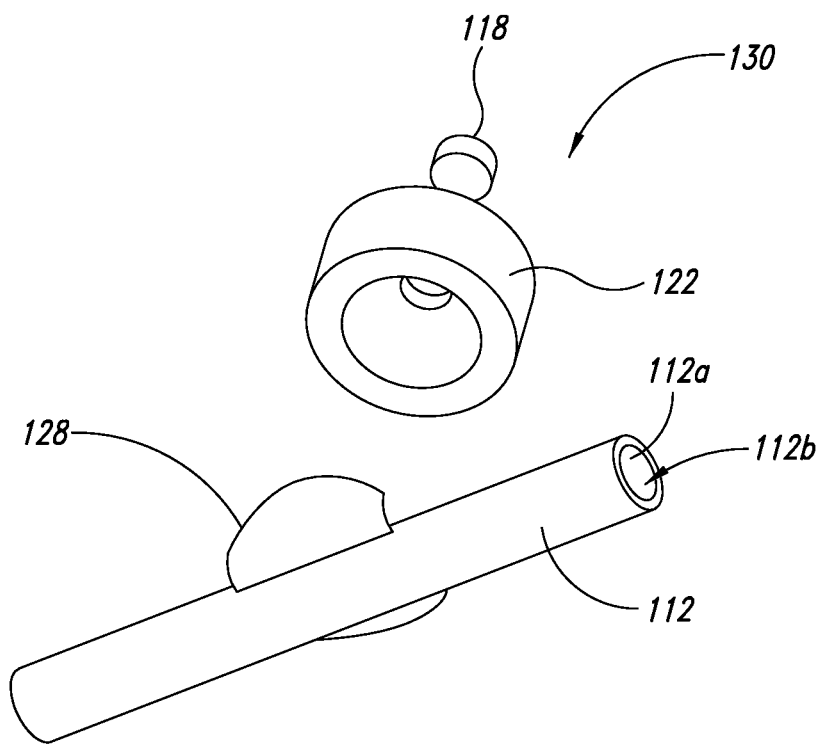
FIG. 5 is an isometric view of an excitation chamber and corresponding mounting element, and an energy-emitting element in the form of a light emitting excitation carried by a heat sink element according to multiple illustrated embodiments.
Figure 6:
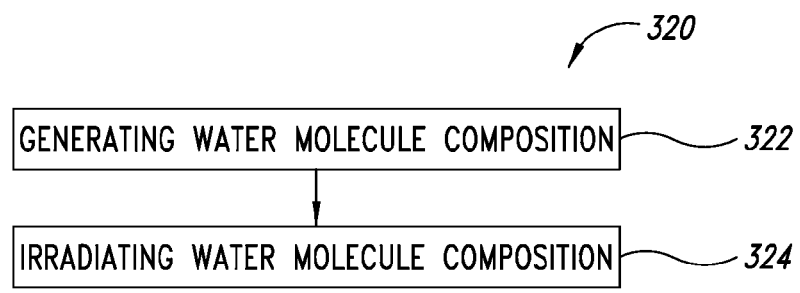
FIG. 6 is a flow diagram of a method of forming an energized water composition according to one illustrated embodiment.

FIGS. 3 through 5 show the embodiments in which the excitation chamber 112 takes the form of a quartz ($SiO_2$) conduit that seats in a mounting element 128 and is carried by housing 114. In some embodiments, the quartz conduit 112 is about 40 mm long cylinder including an outside diameter of 4 mm and interior diameter of 3 mm. The mounting bolts 116 (25 mm M3) may attach the excitation chamber 112 to a base (not shown) and to additional heat sink elements or a fan. In some embodiments, a thermo electric cooler (TEC) takes the place of the heat sink element or fan and may be thermodynamically coupled to the one or more energy-emitting elements 118.

In some embodiments, the entrance of the excitation chamber 112 includes a nozzle that directs the air stream of the water molecule composition directly into the interior of the excitation chamber. The temperature of the nozzle may be controlled to ensure an optimal relationship between, for example, the flow of the water molecule composition and the relative humidity thereof. Other forms of excitation chamber 112 can be used including for example those made from optical spectra (e.g., visible, near Infrared (NIR), infrared (IR), and the like) transmitting materials such as $MgF_2$ or sapphire, plastic, glass, and the like. Other forms of optical excitation energy include IR-VIS-UV spectrum, as well as broad band excitation sources such as a halogen or xenon source.

In another embodiment the water molecule composition is directed through a cooling and condensing nozzle. As they enter the excitation chamber 112 they have an expanding wave form. This expanding waveform allows the molecules to separate into nano-size droplets. Excitation of liquid water has absorption peaks such as approximate centers close to 1200 nm and 2900 nm. These correspond to three main types of vibrations in the OH bonds. These are the symmetric stretch, the asymmetric stretch, and bending.

The excitation chamber 112 may take any geometric form including but not limited to, for example, cylindrical, conical, regular, or irregular forms. In some embodiments, the excitation chamber 112 takes a substantially cylindrical geometric form having a cross-section of substantially any shape including but not limited to circular, triangular, square, rectangular polygonal, and the like, as well as other symmetrical and asymmetrical shapes, or combinations thereof.

Control System

Factors such as the number and size of water droplets, the temperature and humidity of the water molecule composition that are in the field of excitation will determine the efficiency of the system describe herein. Accordingly, controls are set up to allow a user to actively and directly maintain the temperature of the air flow, the temperature of the excitation device, the number and size of water droplets, the irradiant power output, the speed of the airflow and the timing of excitation cycle.

Thus, the control system is a logic system which employs sensors for output excitation, air flow, temperature or water droplet content and size to optimize the output. Depending on the end use of the energized water, the control system may further include feedback sensors such as biofeedback sensors from an individual that is subjected to a treatment by the energized water.

Referring to FIG. 1, the control system 200 may include one or more controllers 202 such as a microprocessor 220*a*, a digital signal processor (DSP) (not shown), an application-specific integrated circuit (ASIC) (not shown), field programmable gate array (FPGA), and the like and may include discrete digital and/or analog circuit elements or electronics. The control system 200 may include one or more memories 204 that store instructions and/or data, for example, read-only memory (ROM) 206 random access memory (RAM) 208, and the like, coupled to the controller 202 by one or more busses 210. The control system 200 may further include one or more input/output devices 212 including, for example a display 214, a keypad (not shown), a switch (not shown), a dial (not shown), a controller module 218 including one or more treatment controller modules 218*a*, 218*b*, and the like, or any peripheral device. In some embodiments, the control system 200 is configured to compare a physiological characteristic of a biological entity to a database 220 of stored reference values, and to generate a response based in part on the comparison.

In some embodiments, the control system is operable to control one or more controllers (e.g., feedback controllers, feedforward controllers, and the like) operable to monitor and or maintain a consistent level of excitation, to select one or more excitation wavelengths, humidity, pressure, or temperature, or combinations thereof, is maintained, regardless of ambient conditions.

The system 10 may further include a power source 222. In some embodiments, the system 10 may include a rechargeable power source in the form of at least one of a button cell, a chemical battery cell, a fuel cell, a secondary cell, a lithium ion cell, a nickel metal hydride cell, a super-capacitor, a thin film secondary cell, an ultra-capacitor, a zinc air cell, and the like. In one embodiment, for example, the system 10 includes an internal battery pack sufficient to power all elements of system 10. In some embodiments, the system 10 may be powered via a conventional electrical wall socket.

In some embodiments, sensors 276 may be placed at various places throughout the system to provide data that would allow a control system 200 to compensate for changes (e.g., temperature changes, flow rate changes, relative humidity changes, and the like). The control system 200 is employed to control the output power of the system 10 in accordance with biofeedback sensors from the biological subject. Such control may involve adjusting, for example, output excitation, single or combination of excitation wavelength(s), duration and intensity of irradiation, pulsing pattern of the irradiation, air flow, temperature, and water droplet content and size. The output can be varied over a cycle of use to respond to a particular end use of the energized water, for example, to a biological subject's measured or desired response.

Optional Components

Referring to FIG. 1, in some embodiments, a fluid management system 250 may be communicatively coupled (e.g., fluidically coupled) to the interior 112*b* of the substantially optically transparent excitation chamber 112 and may be operable to provide or direct a flow of the generated water aerosol or water vapor from the humidifying apparatus 150 through the interior 112*b* of the excitation apparatus 100.

In some embodiments, the fluid management system 250 may include one or more pumps operable to provide a continuous flow of gas to the humidifying apparatus 150 and onward to the excitation chamber 112 and ultimately as to a delivery pump for delivering (e.g., administering) the excited state water structures and/or the water molecule compositions. In some embodiments, the one or more pumps may comprise a 12 VDC, continuous operation diaphragm pump 6 LPM/1.3 bar. The pump may include a motor and diaphragm.

In some embodiments, the pump includes an adjustable flow rate to, for example, ensure calibration. The pumps may also include a muffler to reduce noise and vibration along gas source delivery conduits. In some embodiments, the pump may be placed to draw fluid and gas together in various locations along the fluid conduits of the system 10.

In some embodiments, the one or more sensors 276 are operable to determine at least one physiological characteristic of the biological subject. The control system 200 is communicatively coupled to the one or more sensors 276 and is configured to perform a comparison of the determined at least one physiological characteristic of the biological entity to stored reference data, and to generate a response based in part on the comparison.

In use, a gas stream is directed by the fluid management system including a pump to be mixed with fluid of a water vapor saturation mixer that may form part of the humidifying apparatus 150, and further directed through the excitation chamber 112 and to the biological subject.

In some embodiments, the pump draws both the gas and fluid or partially mixed fluid, and the final mixing takes place in the excitation chamber. In some embodiments, the pump draws gas and then mixes the gas with an additional gas and fluid using vacuum, pressure, or venturi capabilities The disclosed systems, device, methods, or compositions may be operated according to multiple delivery regimens, treatment sessions, and/or therapeutic protocols. For example, the variables as described above can be manipulated to respond in the form of intervals. Interval output involves alternating high intensity excitation with recovery periods. One option is to provide measured periods of work or excitation followed by measured periods of rest. An example would be 1 minute of high intensity excitation, followed by 2 minutes of low intensity excitation and alternating that in a fix or random manner several times for 15-30 minutes. The timing could be preset, controlled manually, or controlled automatically in response to measurements indicative of the biological subject's condition. The measurement of heart rate, respiratory rate, temperature, and/or blood pressure is an example of a condition that might be used in a control cycle. Intervals can also be set that are not responsive to measured conditions, but are controlled by a biological subject during a session.

In another embodiment the control system 200 may monitor the pump, the excitation source, the temperature of the system or flow, the humidity, and any inputs or outputs such as biofeedback and may correct an output of the device and display the variables on a display (e.g., computer screen or LCD panel). In some embodiments, the display may be used to provide real time visual information or visual stimulus or other types of therapeutic information such as biofeedback graphs that might be useful in managing a session.

B. Method of Forming Energized Water

In another embodiment, the present disclosure is directed to a method of forming an energized water composition, comprising: generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; and directing an electromagnetic radiation to irradiate the water molecule composition.

As used herein, directing the electromagnetic radiation includes controlling, selecting, and/or combining one or more electromagnetic energy outputs (characterized by parameters such as wavelength, intensity, intermittency, duration, etc) created by the energy-emitting element 118. The water molecule composition is therefore directly irradiated by the energy-emitting element 118.

FIG. 6 shows a flow diagram to illustrate a method 320 of forming an energized water composition.

At 322, step 300 includes generating a water molecule composition in a carrier gas. In certain specific embodiments, the carrier gas is selected from the group consisting of air, argon, nitrogen, and oxygen. In other embodiments, the water molecule composition further comprises one or more active agents, salts, minerals, vitamins, or a combination thereof.

At 324, step 320 includes directly irradiating the water molecule composition generated in step 300 with a sufficient amount of electromagnetic energy to modify hydrogen bond network of the water molecules.

In certain embodiments, the irradiating step comprises irradiating the water molecule composition at one or more peak emission wavelengths in the optical range including infrared, visible, or ultraviolet spectrum, or combinations thereof.

In other embodiments, the irradiating step comprises irradiating the water molecule composition at one or more peak emission wavelengths in non-optical range including thermal, microwave, nuclear magnetic resonance, or a combination thereof.

In further embodiments, the irradiating step comprises irradiating the water molecule composition at a wavelength selected from 520 nm, 640 nm, 1200 nm and 2900 nm.

In further embodiments, the irradiating step comprises irradiating the water molecule composition at a wavelength selected from 400-600 nm; 550-750 nm; 700-900 nm; 850-1050 nm; 1000-1200 nm; 1150-1350 nm; 1300-1500 nm; 1450-1650 nm; 1600-1800 nm; 1750-1950 nm; 1900-2100 nm; 2050-2250 nm; 2200-2400 nm; 2350-2550 nm; 2500-2700 nm; 2650-2850 nm; 2800-3000 nm; 2950-3150 nm; 3100-3300 nm; 3250-3450 nm; 3400-3600 nm; 3550-3750 nm; 3700-3900 nm; 3850-4050 nm; 4000-4200 nm; 4150-4350 nm; 4300-4500 nm; 4450-4650 nm; 4600-4800 nm; 4750-4950 nm; 4900-5100 nm, and 5050-7000 nm.

In a more specific embodiment, the irradiating step comprises irradiating the water molecule composition at wavelengths of 640 nm and 1200 nm. In another specific embodiment, the irradiating step comprises irradiating the water molecule composition at wavelengths of 520 nm, 640 nm and 1200 nm.

In further embodiments, the irradiating step comprises irradiating the water molecule composition ranging from about 1 nanosecond to 60 seconds.

In further embodiments, the irradiating step comprises irradiating the water molecule composition in an intermittent or pulsing pattern.

In certain embodiments, the irradiating of the water molecule composition generates surface interface structures thereby modifying hydrogen bonding behavior of the water molecules (e.g., at an interface between the water droplets and the carrier gas). In certain embodiments, the modification of the hydrogen bond network elicits changes in pH, redox potential or electrostatic charges, or combination thereof at the interface. Such modification of hydrogen bond network at the interface has significant implications in affecting the properties of surrounding non-energized molecules.

C. Method of Using Energized Water

Water plays an essential role in many chemical and biological processes. The role of water is often represented, however, by a limited number of molecules in a highly restricted molecular environment. Stability, structure, and function of proteins are largely determined by only a few surrounding layers of water molecules in a confined geometry. When the water molecules participate directly in a reaction, the number of involved water molecules is even smaller. For example, the movement of protons across membranes involves the hydrogen network including amino acids and a few confined water molecules. Intracellular water clustered with hydrated biomolecules gives hydrogen bonding networks a greater surface tension than free moving bulk water.

The excitation of water molecules, especially the energizing of the hydrogen bonds has the ability to transfer this energy to enhance the extra cellular communications channels in a biological subject. Such energy transfer could modulate or modify protein functions, impact healing, reduce bacterial and virus proliferation, support the immune system and ultimately activate cellular gating to bolster cellular metabolism and may also impact athletic performance, reduce oxidative stress, and induce a general sense of well being. The delivery of this energy is dependent upon ionic balance, humidity, source energy characteristics, temperature, and time.

Protein Modulation

As discussed herein, water molecule compositions treated with electromagnetic stimulation form excited state structures (e.g., clathrate structures) at the interface of water and air. Such energized water have dynamic hydrogen bond network, which can in turn influence non-treated molecules by transferring and distributing the effects to them, resulting in a modification of the function, properties (pH value, redox potential, etc) and structure of the non-treated molecules. The effects can have therapeutic impact on biological cells. As used herein, "therapeutic" generally refers to a therapeutic process which may be used in the treatment (including the prevention, diagnosis, alleviation, or cure) of a malady, affliction, condition, disease or injury in a biological subject. The effect could be applied to exert a biological response in vitro and/or in vivo.

Biological cells are compartments, inside of which up to several thousand chemical reactions (e.g., metabolism) could occur in any given moment. Some of these intracellular chemical reactions include reactions involving oxygen. These redox reactions, i.e., oxidation reactions and reduction reactions, change the status of the cellular environment. Thus, the value of the redox potential is indicative of certain status of a biological environment. It is known that any intracellular redox reactions influence other substances that are potentially redox-sensitive within that environment. In other words, any change in the intracellular redox potential has an influence on redox-sensitive intracellular substances. Redox-sensitive components in biological cells include proteins and the hydrogen bond network.

Influences in the change of redox potential could lead to a dysfunction or improvement of a function of the exposed components. In cell biology, it is known that protein denaturation can be caused by changes of the redox potential. On the other hand, certain protein functions are favorably amplified by changes of the redox potential. The same phenomenon is known to influence the function of the hydrogen bond network and other redox-sensitive components.

Besides the intracellular redox reactions, factors external to the cell also affect the redox potential of a biological cell. Chemical composition, pH value, conductivity, rate of saturation as well as the hydrogen bond structure itself can be modified by external influences, such as the influences created by energized water.

Because the energized water generated in accordance with the disclosure can cause changes in pH values, conductivity, hydrogen bonding behavior and redox potentials in its excited state structures, it may be used to modify or modulate protein functions (e.g., signal transduction), thereby providing therapeutic treatment for cancer, immune and autoimmune deficiencies, metabolic disorders, sleep apnea, oxidative stress caused diseases, cardiovascular disorders, COPD, asthma, diabetes, macular degeneration, Alzheimer's disease, Parkinson's disease and others.

Thus, one embodiment provides a method for modulating protein functions in a biological subject. The method includes generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and contacting the energized water with the biological subject.

In some embodiments, directing an electromagnetic radiation to irradiate the water molecule composition includes providing a sufficient amount of electromagnetic energy having one or more wavelengths in the range of about 10 nm to about $1\times10^6$ nm to the water molecule composition that result in the formation of one or more clathrate structures or clustered structures within the water droplets.

In other embodiments, directing an electromagnetic radiation to irradiate the water molecule composition includes providing a sufficient amount of electromagnetic energy having one or more wavelengths in the range of about 10 nm to about $1\times10^6$ nm to the water molecule composition that causes a pH change in the water molecule composition.

In further embodiments, directing an electromagnetic radiation to irradiate the water molecule composition includes providing a sufficient amount of electromagnetic energy having one or more wavelengths in the range of about 10 nm to about $1\times10^6$ nm to the water molecule composition that causes a redox potential change in the water molecule composition.

In further embodiments, directing an electromagnetic radiation to irradiate the water molecule composition includes irradiating the water molecule composition at a wavelength selected from 520 nm, 640 nm, 1200 nm and 2900 nm.

In a more specific embodiment, directing an electromagnetic radiation to irradiate the water molecule composition includes irradiating the water molecule composition at wavelengths of 640 nm and 1200 nm. In another specific embodiment, the irradiating step comprises irradiating the water molecule composition at wavelengths of 520 nm, 640 nm and 1200 nm.

In further embodiments, directing an electromagnetic radiation to irradiate the water molecule composition includes irradiating the water molecule composition ranging from about 1 nanosecond to 60 seconds.

In further embodiments, directing an electromagnetic radiation to irradiate the water molecule composition includes irradiating the water molecule composition in an intermittent or pulsing pattern.

In some embodiments, contacting the energized water with the biological subject alters a redox potential in a cellular reaction.

In certain embodiments, contacting the energized water with the biological subject comprises directing the energized water through a passage way into the biological subject. In one embodiment, the energized water can be delivered through air passage ways, e.g., through inhaling or a respirator.

In some embodiments, contacting the energized water with the biological subject includes administering the energized water molecule composition via ingestion. In some embodiments, contacting the energized water with the biological subject includes transdermally delivering the activated water molecule composition. In some embodiments, contacting the energized water with the biological subject includes contacting an opening in the skin (e.g., an open wound) of the biological subject.

In various specific embodiments, the method described herein provides energized water to modify membrane proteins.

Individual water molecules play central structural and functional roles in proteins, such as in proton transfer reactions. A pH gradient across a membrane influences the proton transfer because of their electrostatic interactions within the protein. Membrane proteins constitute about one third of the human genome and play diverse biological roles in processes such as biological energy transduction, transport of ions and polar compounds, pH regulation, signal transduction, and vesicle fusion. Interactions such as proton binding sites in a molecule, can deviate depending on their pH-titration which can be described by the Henderson-Hasselbalch equation. Biochemical processes depend on the ability of proteins to interact with nucleic acids, lipids, polysaccharides, substrate molecules, and each other. Specific molecular recognition is a prerequisite for electron transfer between redox partners, antigen recognition by the immune system, for signal transduction in cells, for the adaptation of cells to environmental conditions, and for many other physiological reactions.

One example of the importance is the binding of small ligands and ions such as protons to a protein (i.e., the pH titration of a protein). Structural changes that occur upon reduction can also be triggered by changing the pH. This coupling between electron and proton transfer fundamental to bio-energetic reactions. Often the energy of an energetically favorable electron transfer reaction is used to drive an energetically unfavorable proton transfer across a membrane. This coupling between electron and proton transfer can be facilitated by electrostatic interaction. The reduction of a redox-active group causes the protonation of adjacent groups. Such a mechanism is known for many proteins and termed redox-Bohr effect.

Water molecules ionize endothermically due to electric field fluctuations caused by nearby dipole librations resulting from thermal effects, and favorable localized hydrogen bonding; a process that is facilitated by exciting the O—H stretch overtone vibration. As shown in Eq. 1:

$$2H_2O \rightarrow H_3O^+ + OH^- \quad \text{(Eq. 1)}.$$

ions are separate by, for example, means of the Grotthuss mechanism but normally recombine within a few femtoseconds. These ions may create order and may form stronger hydrogen bonds with surrounding water molecules. Changes in hydrogen bonding caused by clathrate formation may encourage ionization. Given that clathrate-like structures are likely a part of the normal structure of water and that excitation of hydrogen bonds will likely lead to bonds reforming in a clathrate form, it follows that the resultant presence of ions at the surface will have an effect on the apparent local pH and electrostatic potentials. Hydronium ions, $H_3O^+$ inversion may require less energy than reforming hydrogen bonds which also suggests an alternative to rotation within hydrogen bonded clusters. The presence of an $H_3O^+$ ion has been measured to affect the hydrogen bonding of at least 100 surrounding water molecules. This ion is very stable in liquid water. Once correctly oriented, the potential energy barrier to proton transfer is believed to be very small. After a proton has moved along a chain of water molecules, a reorientation of the hydrogen bonding must occur if similar proton movement is to proceed. Lung tissue has a high demand for water movement, and in the case of aquaporins, millions of water molecules can be in direct transit through these tissue water channels. In some cases, aquaporins can control the movement of protons through their water channels. In this case, water molecules are deliberately re-oriented to preclude sequential hydrogen bonding so prevent proton transfer by the Grotthuss mechanism. Ion selectivity of the sodium channel may be affected by the size of the ion when it is hydrated by one or more water molecules.

Three kinds of membrane proteins have been shown to have water channels properties including aquaporins, cotransporters, and uniports. A molecular-kinetic description can be made based on macroscopic parameters such as pore size and thermodynamics. The influence of hydrogen bonds between solute and pore, and the pH dependence of permeability demonstrate the importance of, for example, the electrostatic effect. A realistic description of water transport can be made. Water movement is related to solute permeability of cotransporters and uniports as substrate transporters.

The main function of the lung is to allow transfer of oxygen and carbon dioxide molecules across the alveolar-capillary membrane. In order to achieve this task most efficiently, the lung must free itself of excess liquid, proteins, and other debris. Under normal conditions, there is continuous leakage of water from the alveolar capillaries into the interstitial space, which is eventually reabsorbed and restored to the circulation.

Aquaporins have to be highly specific for water to prevent other solutes and ions from also crossing the membrane. In this respect, protons present a particularly difficult challenge, because the positive charge of a proton can move along a column of water by hydrogen bond exchange. Since proton fluxes across cellular membranes drive physiological processes, such as membrane fusion, vesicular transport, solute transport, and ATP synthesis, proton leakage across the membrane must be avoided.

Blocking proton transfer is believed to require interruption of the continuous chain of hydrogen bonds along a single file of water by hydrogen-binding sites at the pore surface. In some embodiments, the interactions of the membrane with neighboring water molecules may cause a reorientation of the water molecules. For example, the oxygen atom of the water molecule may reorient to form hydrogen bonds with amido groups. This reorients the two hydrogen atoms of the water molecule which are prevented from forming hydrogen bonds with adjacent water molecules in the single-file column. The water molecule in the pore constriction can form hydrogen bonds via oxygen but not through hydrogen atoms. Thus, water molecules can permeate the pore with a minimal energy barrier, whereas transfer of protons is blocked by hydrogen-bond isolation from bulk water.

A large proportion of internal surface area of the lung is lined by alveolar epithelial cells. Water permeability between the airspace and vasculature in the lungs is high and water movement across the interface of airspace and lung vasculature is required to maintain the normal state of physiological processes. Water movement also may be important in maintaining lung water homeostasis. Alveolar $O_2$ diffuses toward the exchange surface 1.2 times faster than $CO_2$ leaves the exchange surface and a high water solubility coefficient promotes diffusion. Gases must be carried away to maintain local diffusion gradients in the lung. Osmotic water permeability in type I cells is also weakly temperature dependent.

Between the air and the vasculature there are epithelial, interstitial, and endothelial compartments. The alveolar epithelium, which covers more than 99% of the internal surface area of the lungs is comprised of a monolayer of two morphologically distinct types of cells, type I cells and type II cells. The very thin cytoplasmic extensions of type I cells cover 95-98% of the surface area of the lung. Type II cells, which cover the remaining 2-5% of the alveolar surface, are best known for their ability to synthesize, secrete, and recycle components of pulmonary surfactant. The interstitial compartment varies considerably in thickness. At its thinnest, the alveolar epithelium is separated from capillary endothelium only by a fused membrane. Intercellular tight junctions between alveolar epithelial cells are thought to provide a tight barrier between the air and blood compartments of the lung. Based on these anatomic considerations, it is thought that alveolar epithelial type I cells might play an important role in water transport. Recent data indicate that water moves rapidly between the airspace and capillaries in response to osmotic gradients. This is facilitated by a transcellular route for water movement through molecular water channels (aquaporins). A number of aquaporins have been evaluated in lung tissue including: AQP1 in capillary endothelia and some pneumocytes; AQP4 in basolateral membranes of airway epithelium; and AQP5 in apical membranes of alveolar epithelium. But the importance of these individual aquaporins in normal lung function is not known.

Studies of epithelial ion and fluid transport across the distal pulmonary epithelia have provided evidence that vectorial ion transport across the alveolar and distal airway epithelia is a primary determinant of alveolar fluid clearance (AFC). Reduced levels of surfactant protein have also been related to patient outcomes with lung disorders. Active $Na^+$ and $Cl^-$ transport drives are also critical to net alveolar fluid clearance, as demonstrated in several different species, including the human lung.

In the lung, as in other epithelia, ion transporters and other membrane proteins are asymmetrically distributed on opposing cell surfaces, conferring vectorial transport properties to the polarized epithelial cells. Tight junctions populate these epithelial cells near their apical surfaces, thereby sustaining apical and basolateral cell polarity. The permeability of tight junctions is dynamic and regulated, in part, by cytoskeletal proteins and intracellular Ca concentrations and by ion channels.

Stress on the lung processes may be caused by issues of protein hydration, boundary layer surfactants, aquaporin water transfer, fluid build up, and vapor/water surface tension boundaries. It is known that water vapor and small clusters act in different ways on lung tissue due to their surface tension. The vibrational dynamics of water interfaces and interfacial bonded OH stretch modes can demonstrate various behaviors. The variations in clathedic alignment can change the positions of free ions such that surface tension, surface pH, and electrostatic potentials will vary. Excitation of water is one source of such activity and its resultant vibrational lifetime will vary depending on the source of excitation and the phase state of the water. Vibrational excitation is followed by spectral diffusion, vibrational relaxation, bond realignments, electrostatic changes, polarization, clathrate alignment, and thermalization in the hydrogen-bonding network, all which have different time domains dependent upon the ambient conditions such as temperature, electric fields, humidity, pressure, and proximity to other large droplets or bulk water. One peculiarity of the liquid state of water is the nonequivalence of O—H groups of water molecules in hydrogen bonding. The structure of liquid water and the mechanism of its molecular mobility must be considered in this context.

The organization of lipid and other insoluble surfactant monolayers at the air-water interface under equilibrium conditions is well known, as the subject has been of great interest in biology, chemistry, and physics for nearly a century. Less is known about the dynamic and stressed aspects of monolayer structure and functions, especially monolayer failure, which ultimately limits the surface tension reduction possible by a given monolayer.

Native lung surfactant extracts adsorb to air/water interfaces rapidly to form monolayers. The lung surfactant monolayer is initially fluid-like at large areas per molecule. On compression, lung surfactant monolayers achieve near-zero surface tension. At low-ionic strength, these aggregates apparently diffuse away from the monolayer and remain in the subphase. At high-ionic strength, the alveolar structures (vesicles) remain attached to the monolayer (or at least in the immediate vicinity of the monolayer) and rapidly reincorporate into the monolayer on expansion of the film.

The charged domains of the multicomponent lung surfactants have a large Debye length or low subphase ionic strength and there is an electrostatic energy barrier to readsorption of the charged vesicles to the charged interface. In opposition to this electrostatic repulsion are a complicated set of hydrophobic, Van der Waals, and other attractive interactions that promote readsorption of the bilayer aggregates to the interface.

Surface pressure and phase behavior are related to the strength of these attractive interactions. Interactions with the monolayer depend on the magnitude of the electrostatic repulsion, which scales with the Debye length, or the distance relative to charge separation. At low salt concentrations, the Debye length is large, and vesicles diffuse away from the monolayer. At higher salt concentrations, the Debye length is small, and the interaction can even become attractive.

The interaction depends on the strength of the electrostatic interactions, as the attractive interactions between bilayers are much less dependent on ionic strength. Ionic strength, pH, and electrostatic interaction will have an effect on the health and optimal function of the alveolar gas/liquid interface. If the electrostatic barrier is such that the attractive interactions dominate, the rate or readsorption is enhanced, and more vesicles readsorb before they diffuse away into the subphase. The multicomponent lipid and protein lung surfactant monolayers may be enhanced or inhibited in relation to adsorption and respreading. A broad range of hydrophilic, nonionic polymers, including polyethylene glycols, dextrans, of widely varying molecular weights enable surfactants to work optimally.

Such polymers are known to dehydrate multilamellar lamellar phases, or induce a depletion attraction between aggregates and a surface, thereby making bilayer aggregates less stable and/or changing the height of the energy barrier. Some cationic surfactant specific proteins might provide ways around the energy barrier as they form multilayer patches that may provide locally, net positive charged docking sites for anionic surfactant adsorption. Specific proteins locate preferentially in anionic and/or fluid bilayers as well. These docking sites for readsorption suggest that it is the multiple cationic residues of these proteins that assist with stressed function.

Stress on the lung processes may be caused by issues of protein hydration, boundary layer surfactants, aquaporin water transfer, fluid build up, and vapor/water surface tension boundaries.

The flux of respiratory gases across the tissue barriers occurs entirely by passive diffusion along established partial pressure differences. In conformity with the physics of a passive process, the structural properties of the barrier influence the rate and efficiency of gas transfer. The diffusing capacity, or the conductance of the tissue barrier for oxygen for instance, correlates directly with the surface area and inversely with the thickness of the partition. The lung works to maintain a persistent balance between the forces that move water into the extravascular spaces and the biologic devices for its removal, to exchange gases and to remove proteins, contaminants, and pathogens from its surface.

The tissue interface is essentially comprised of a thin epithelial cell that faces water/air, an extracellular matrix/interstitial space, and an endothelial cell that fronts the blood capillary, whereby the design of the water-blood-gas barrier is highly conserved.

States and factors such as the degree of inflation, perfusion pressure, surface tension, and hydrostatic pressure determine the structure and organization of the connective tissue scaffold of the lung parenchyma. The relationship between epithelial fluid transport, standing osmotic gradients, and standing hydrostatic pressure gradients assumes that the volume of lateral intercellular space per unit volume of epithelium is small and the membrane osmotic permeability is greater than the solute permeability.

The rate of fluid reabsorption is set by the rate of active solute transport across lateral membranes. The fluid that crosses the lateral membranes and enters the intercellular cleft is driven longitudinally by small gradients in hydrostatic pressure and molecular kinetics. The small hydrostatic pressure in the intercellular space is capable of causing significant transmembrane fluid movement; however, the transmembrane effect is countered by the presence of a small standing osmotic gradient.

Longitudinal hydrostatic and osmotic gradients balance such that their combined effect on transmembrane fluid flow is zero, whereas longitudinal flow is driven by the hydrostatic gradient. Because of this balance, standing gradients within intercellular clefts are effectively uncoupled from the rate of fluid reabsorption, which is driven by small, localized osmotic gradients within the cells. Water enters the cells across apical membranes and leaves across the lateral intercellular membranes. Fluid that enters the intercellular clefts can, in principle, exit either the basal end or be secreted from the apical end through tight junctions. Fluid flow through tight junctions is shown to depend on a dimensionless parameter, which scales the resistance to solute flow of the entire cleft relative to that of the junction. Estimates of the value of this parameter suggest that an electrically leaky epithelium may be effectively a tight epithelium in regard to fluid flow.

In the normal lung, intricate anatomic arrangements coupled with elaborate physiologic mechanisms maintain the gas-exchanging surfaces moist and free of excess protein. A transient excess of water in the interstitial space is associated with an increase in lymphatic flow. Should the excess rate of formation persist or increase, the homeostasis will be out of balance. The distribution of unbalance within the lung may also be nonuniform, often favoring the central portions early in its genesis but later redistributing under the influence of gravity. A critical limitation in anatomic design is imposed by the narrow channels through which lymph passes out of the thorax into systemic veins. Accordingly, the pulmonary lymphatic system, which seems better suited to return proteins than water to the systemic circulation, may become a limiting factor in relieving stressed states of unremitting water movement into the extravascular spaces.

Recent data indicates that water moves rapidly between the airspace and vasculature in response to osmotic gradients. A major function of type I cells may be the maintenance of a water permselective physical barrier. The high water permeability between the airspace and vascular compartments in the lung suggests the involvement of molecular water channels (aquaporins) in water transport. The type I cells may play an important role in the high water permeability between the airspace and vasculature of the lung. The high water permeability of type I cells, and water channel functional requirements in the lung, demonstrate the important role for aquaporin-type water channels in lung physiology.

Water channels are expressed strongly in airway and alveolar epithelial and endothelial plasma membranes, water permeability is high across alveolar and airway epithelia, and lung water channel expression and function are developmentally regulated.

Thus, in one embodiment, the present disclosure is directed to a method of affecting a physiologic process of a biological subject associated with aquaporin-mediated water transport. The method includes generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and delivering the energized water to a region of the biological subject associated with aquaporins.

Figure 7:
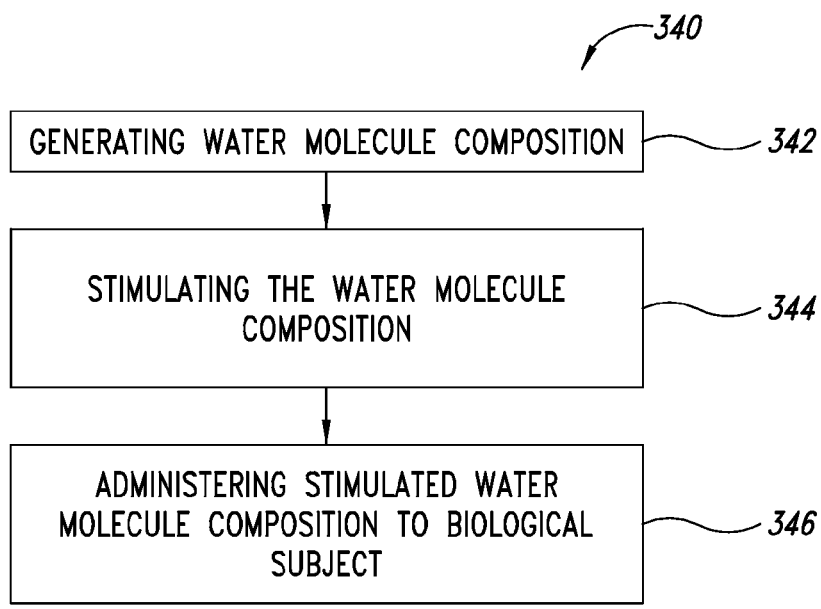
FIG. 7 is a flow diagram of a method of affecting a physiologic process of a biological subject associated with aquaporin-mediated water transport according to one illustrated embodiment.

FIG. 7 shows an exemplary method 340 affecting a physiologic process of a biological subject associated with aquaporin-mediated water transport.

At 342, the method 340 includes generating a water molecule composition in a carrier gas, the water molecule composition being a water aerosol composition, water vapor, or a combination thereof, the water aerosol composition comprising water droplets of nano-size, micron-size or a combination thereof. In certain specific embodiments, the carrier gas is selected from the group consisting of air, argon, nitrogen, and oxygen.

In some embodiments, generating the water molecule composition further comprises generating the water molecule composition including salts, minerals, vitamins, or one or more active agents selected from the group consisting of a pharmaceutical agent, a neutraceutical, an antioxidants, a phytochemical, and a homeopathic agent.

At 344, the water molecule composition is directed toward a passageway define by an interior surface of an excitation chamber. In some embodiments, the passageway is in communication with an electromagnetic energy source having one or more peak emission wavelengths in the range of about 10 nm to about $1 \times 10^6$ nm. The energy source can be optical or non-optical. In some embodiments, the energy source can be at least one of a laser, a laser diode, a light emitting diode, an arc flashlamp, and a continuous wave bulb.

The water molecule composition is then irradiated using electromagnetic energy having one or more peak emission wavelengths of about 240 nm to 7000 nm. More specifically, the emission wavelengths can be 520 nm, 640 nm, 1200 nm or 2900 nm, or a combination thereof.

At 346, the method 340 includes administering the stimulated water molecule composition to a region of the biological subject associated with aquaporins.

Another embodiment provides a method of affecting hydrogen-bonding process, which includes generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water; and contacting the energized water with molecules that participate in hydrogen bonding.

In certain embodiments, the molecules that participate in hydrogen bonding include biomolecules such as proteins and peptides.

In one embodiment, the water-mediated hydrogen bonding process is associated with signal transduction in an aerobic organism.

As used herein, "signal transduction" refers to changes in biological functions as a result of energy transduction or the exposure to excited state water molecules (e.g., in clathrate structures). For instance, cellular activity is regulated by a complex network of intracellular and extracellular transduction pathways. Energy transfer at the cellular level can refer to the movement of signals from outside the cell to inside or from inside to outside. Energy transduction or signal transduction could mean any change in biophysical properties. For instance, in their normal biological function, proteins may fold into one or more specific spatial conformations, driven by interactions such as hydrogen bonding, ionic interactions, Van der Waals' forces, and hydrophobic packing.

Figure 8:
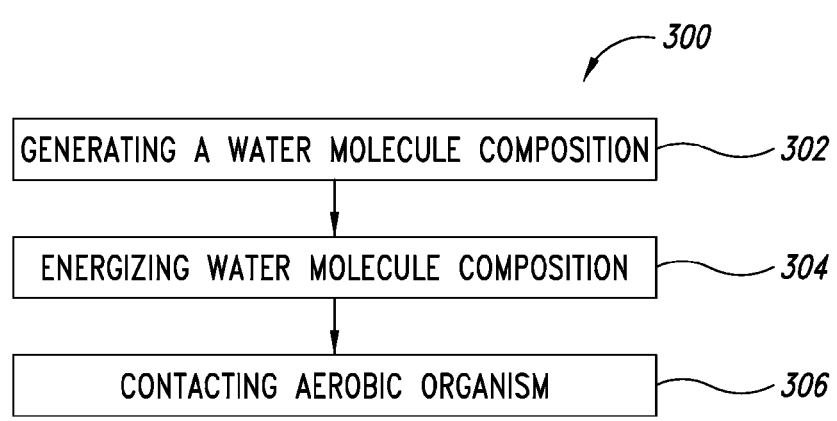
FIG. 8 is a flow diagram of a method of affecting at least one water-mediated hydrogen-bonding process associated with signal transduction in an aerobic organism according to one illustrated embodiment.

FIG. 8 shows an exemplary method 300 of affecting at least one water-mediated hydrogen-bonding process associated with signal transduction in an aerobic organism.

At 302, the method includes generating a water molecule composition in a carrier gas. In certain specific embodiments, the carrier gas is selected from the group consisting of air, argon, nitrogen, and oxygen. In other embodiments, the water molecule composition further comprises one or more active agents, salts, minerals, vitamins, or a combination thereof.

At 304, the method 300 includes directly energizing the water molecule composition by with electromagnetic radiation to provide an energized water molecule composition.

At 306, the method includes contacting the aerobic organism with the energized water molecule composition generated in 304.

Oxidative Stress Reduction

Living cells (e.g., mammalian cells, animal cells, plant cells, and insect cells, as well as various species of bacteria, algae, plankton, and protozoa, and the like) are continuously exposed to reactive oxygen species (ROS) such as, for example, lipid peroxyl, superoxide, hydrogen peroxide hydroxyl radicals, and singlet oxygen. In vivo, these reactive oxygen intermediates are often generated by cells in response to, for example, aerobic metabolism, catabolism of drugs and other xenobiotics, ultraviolet and x-ray radiation, and the respiratory burst of phagocytic cells (e.g., white blood cells) when killing invading bacteria such as those introduced through wounds or as found near the alveolus of the lung tissue. Hydrogen peroxide ($H_2O_2$), for example, is produced during respiration of most living organisms especially by stressed and injured cells.

Excess reactive oxygen species such as, for example, hydrogen peroxide can react with DNA to cause backbone breakage, produce mutations, and alter and liberate bases. Another example of the ability of reactive oxygen species to injure cells is lipid peroxidation, which involves the oxidative degradation of unsaturated lipids. Lipid peroxidation is highly injurious to membrane structure and function and can cause numerous cytopathological effects.

Oxidative stress results in part from an imbalance between the production of the reactive oxygen species and a biological subject's ability to detoxify the reactive intermediates or repair the resulting damage. Oxidative stress may cause cellular damage, resulting in alteration of the redox state (e.g., depletion of nucleotide coenzymes and disturbance of sulfhydryl-containing enzymes), and saturation and destruction of the antioxidant defense and DNA repair system. For example, changes to the normal redox state can in some instances cause toxic effects through the production of peroxides and free radicals that damage cell components including proteins, lipids, and DNA. Such oxidative biochemical injury can result in the loss of cellular membrane integrity, reduced enzyme activity, changes in transport kinetics, changes in membrane lipid content, and leakage of potassium ions, amino acids, and other cellular material. Failure to restore the cellular balance of the level of oxidizing species (e.g., reactive oxygen species and reactive nitrogen species) can result in DNA damage, lipid peroxidation, loss of intracellular calcium homeostasis, and alterations in signal transduction (e.g., cellular signaling) and metabolic pathways.

Oxidative stress has been associated with a variety of diseases and disorders, including aging and neuronal cell death. For example, oxidative stress is associated with the pathology of numerous neurodegenerative diseases and conditions including, but not limited to, Alzheimer's disease, diabetic peripheral neuropathy, multiple sclerosis, amyotrophic lateral sclerosis, Huntington's disease, and Parkinson's disease. Accordingly, there exists a need to improved cellular protection and repair processes in aerobic organisms.

Energized clathrate structures of water that contain partial charges or hydronium ions ($H_3O^+$) are likely to form bonds with hydroxyl radicals and even weaken other hydrogen bonds in their spatial influence. These properties of the hydrogen bonded environment will be particularly evident at the surface of liquid water where charges will reside and more reactive "dangling" O—H groups will be directed away from the surface. Some hydronium ions ($H_3O^+$) also point away from the surface as they only poorly accept hydrogen bonds (but strongly donate three), with their oxygen atom pointing at the surface. This would encourage these ions to sit in the surface layer, so as to combine with ROS (e.g., hydrogen peroxide).

$$H_2O_2 + 2H_3O^+ \rightarrow 4H_2O \qquad \text{(Eq. 2)}$$

Thus, one embodiment provides a method for reducing oxidative stress by combining with ROS to render them less reactive or inactive. The method includes: generating a water molecule composition in a carrier gas, the water molecule composition being a water aerosol composition, water vapor, or a combination thereof, wherein the water aerosol composition comprises water droplets suspended in the carrier gas, the water droplets being of nano-size, micron-size or a combination thereof; directing an electromagnetic radiation to irradiate the water molecule composition, thereby providing energized water that includes hydronium ions at their excited states; and delivering the energized water to a biological subject, whereby the hydronium ions at the excited states of the water are combined with reactive oxygen species.

In some embodiments, generating the water molecule composition further comprises generating the water molecule composition including salts, minerals, vitamins, or one or more active agents selected from the group consisting of a pharmaceutical agent, a neutraceutical, an antioxidants, a phytochemical, and a homeopathic agent.

In various embodiments, directing the electromagnetic radiation to irradiate the water molecule composition comprises irradiating with electromagnetic energy having one or more peak emission wavelengths of about 240 nm to 7000 nm. More specifically, the emission wavelengths can be 520 nm, 640 nm, 1200 nm or 2900 nm, or a combination thereof.

Bulk Water Modification

In a further embodiment, the energized water can be delivered to bulk water to modify the properties thereof. More specifically, when energized water contacts untreated (not energized) bulk water, energy transfer occurs, which may alter properties such as the pH, conductivity, redox potential of the bulk water. The modified bulk water is suitable for drinking, food industry, medicine, agriculture (e.g. irrigation), aquariums, printing, cleaning and paint industries, where untreated bulk water is typically used.

Thus, the method comprises generating a water molecule composition in a carrier gas, the water molecule composition being a water aerosol composition, water vapor, or a combination thereof, wherein the water aerosol composition comprises water droplets suspended in a carrier gas, the water droplets being of nano-size, micron-size or a combination thereof; directing an electromagnetic radiation to irradiate the water molecule composition, thereby providing energized water; and contacting the energized water with bulk water.

In certain embodiments, the energized water are infused into bulk water for a period of time sufficient to change the pH, redox potential and conductivity of the bulk water.

The various embodiments described herein are further illustrated by the following non-limiting examples.

EXAMPLES

Example 1

Changes in pH of Energized Water

Ultra-sensitive fluorescence test was carried out to detect changes in the pH values in energized water droplets as compared to untreated water droplets.

A fluorescence spectrophotometer with a carboxyethyl probe was used (Joule Microsystems). The probe was exposed during a first 9 seconds to an unconditioned (untreated) air stream to allow the fluorescence spectrophotometer calibrates the probe.

After the first 9 seconds, the air stream is energized in accordance with an embodiment described herein. As soon as the excitation (490 nm) begins in the excitation chamber, an immediate, rapid and significant change in the pH value is registered (see, Table 2)

TABLE 2

MEASUREMENT OF OPTICAL FLUORESCENCE TO DETECT PH CHANGES

|  | Untreated Air Stream (without excitation) | Energized Air Stream (With Excitation) |
|---|---|---|
| pH | 0.1481 | 0.1510 |

Example 2

Optical Absorption

Optical absorption test was carried out using a fluorescence spectrophotometer carboxyethyl probe (Joule Microsystems).

The probe was exposed during a first 9 seconds to an unconditioned (untreated) air stream. During the first 9 seconds the fluorescence, the spectro-photometer did not register any wavelength absorption.

Figure 9:
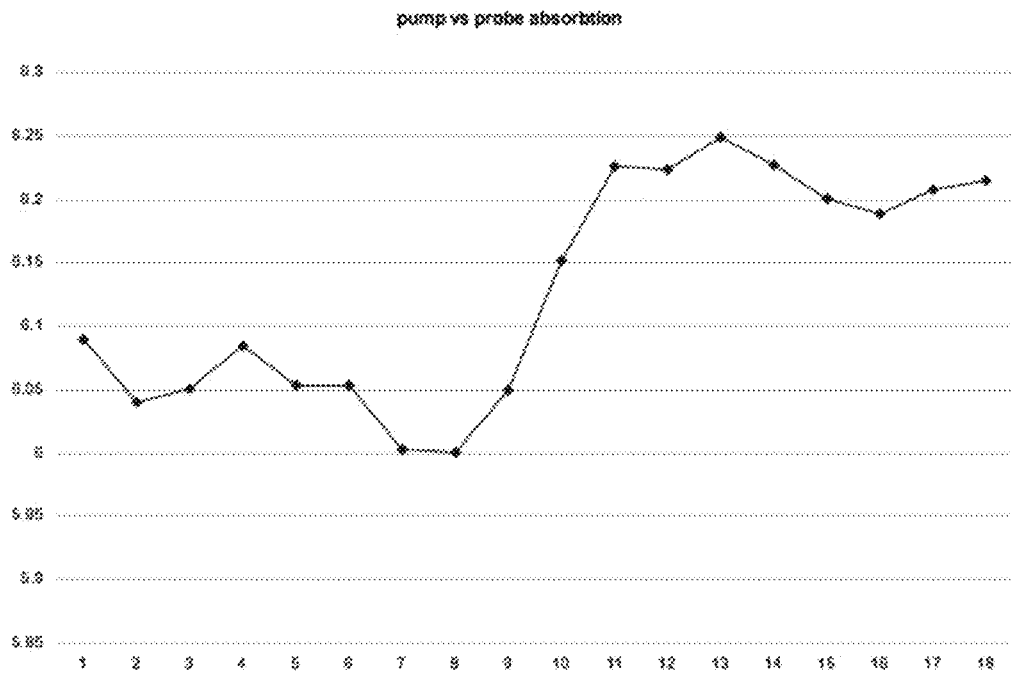
FIG. 9 shows an optical absorption profile of untreated water molecule composition followed by excitation.

Thereafter, the air stream is energized in accordance with an embodiment described herein at 2900 nm, an immediate, rapid and significant wavelength absorption is registered (see, FIG. 9). Table 3 also shows the ratio optical absorption (in an arbitrary unit) of untreated air stream as compared to energized air stream. Absorption was measured at both 595 nm and 640 nm. The ration is the difference in the normalized absorption of 595 nm/640 nm.

TABLE 3

MEASUREMENT OF RATIO OF OPTICAL ABSORPTION

|  | Untreated Air Stream (without excitation) | Energized Air Stream (With excitation) |
|---|---|---|
| Ratio of Optical Absorption | 6.05 | 6.210 |

Example 3

Enzymatic Test

A DNA cleavage test was carried out and the results were observed with a microscope with special observation chamber. Inside the microscope observation chamber, the DNA probes were exposed to an unconditioned air stream and to an air stream energized in accordance with an embodiment disclosed herein. The test was conducted with four different levels of dilution of the DNA probe.

The followings set forth the specific conditions of the test: DNA probe: plasmid pGEM-15-4, Enzyme probe: EcoR1 Exposure time: 30 minutes in 37° C.

Figure 10:
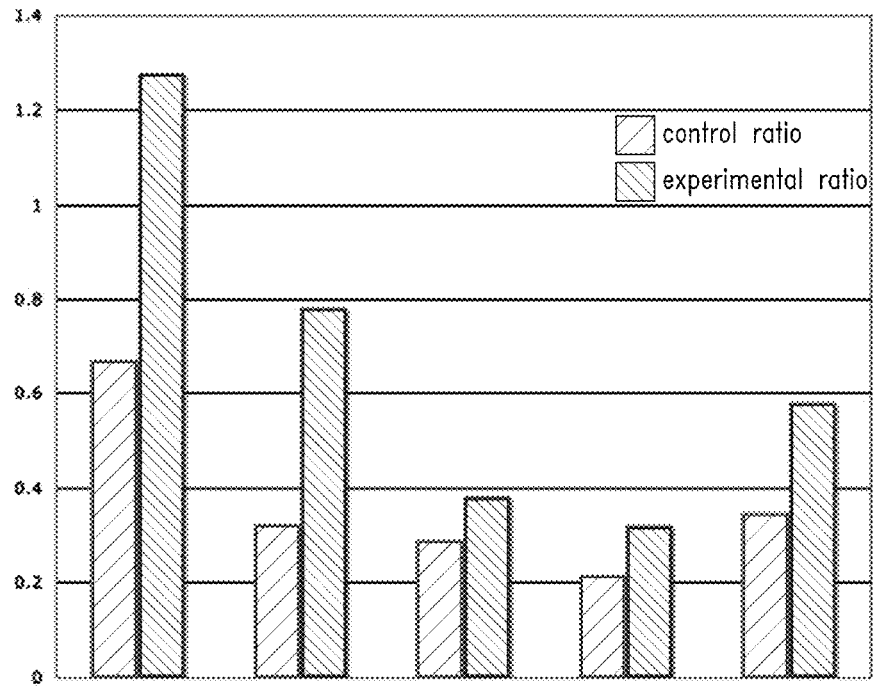
FIG. 10 shows the changes in the enzymatic activity of a DNA probe that has been exposed to energized water.

FIG. 10 shows that, 30 minutes after the DNA probe was exposed to the energized air stream, significant increases in the enzymatic activity (DNA cleavage) were observed. Results were consistent for all four levels of dilution.

Example 4

Energy Transfer

Energy transfer was confirmed by detecting the changes of dielectric potentials of energized air stream as compared to untreated air stream of water droplets.

Untreated and energized air streams were connected to a resistive surface in a dielectric cell.

Figure 11A:
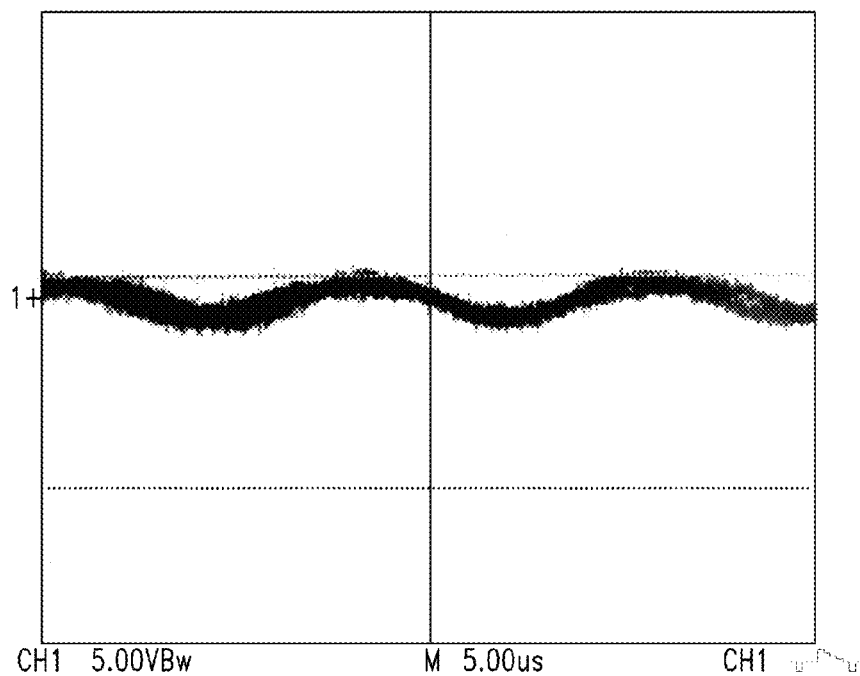
FIGS. 11A-11B show a change in dielectric potential, which is indicative of energy transfer occurred in energized water.
Figure 11B:
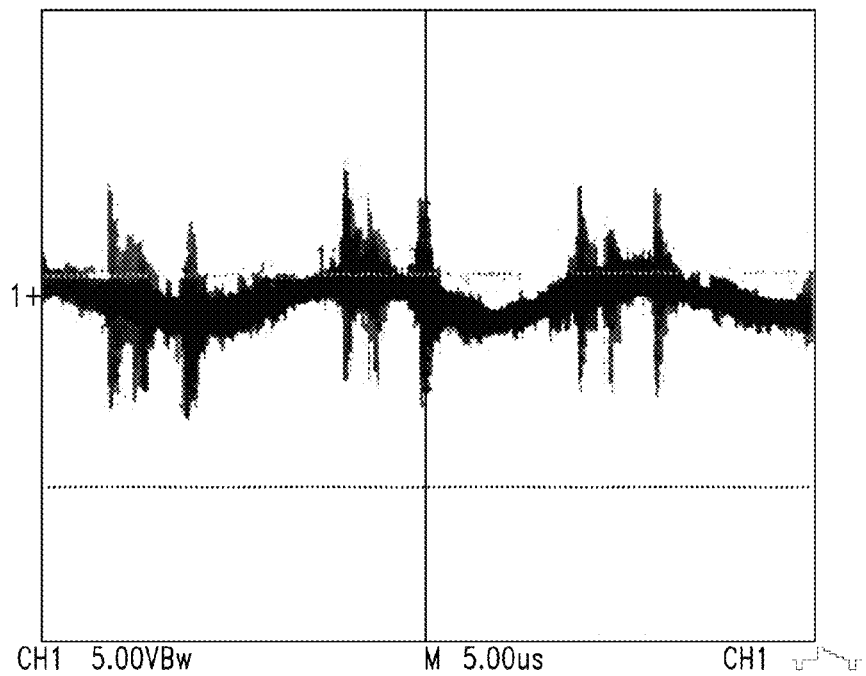

FIGS. 11A-11B show that, within the dielectric cell, a significant change in energy transfer was observed in the energized air stream (FIG. 11B) as compared to the untreated air stream (FIG. 11A).

Example 5

Conductivity Test

Untreated and energized air streams were connected to each of two different test cells. The test cell included two electrodes, semi conductive gel and a 200V pulse was transmitted over the gel.

Figure 12A:
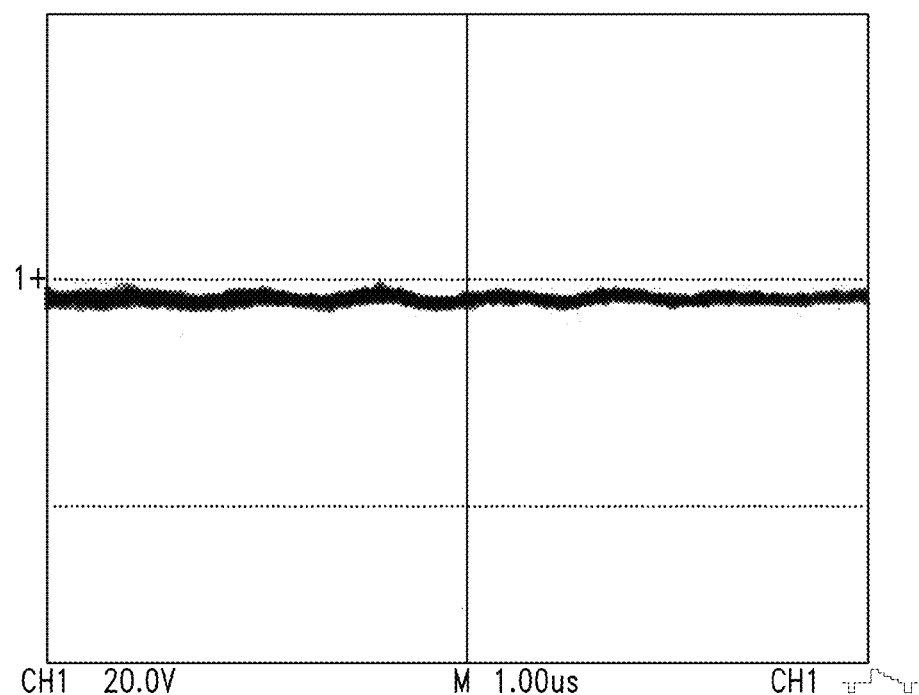
FIG. 12A-12B show a significant change in energy transfer in a conductivity cell for energized water as compared to untreated water.
Figure 12B:
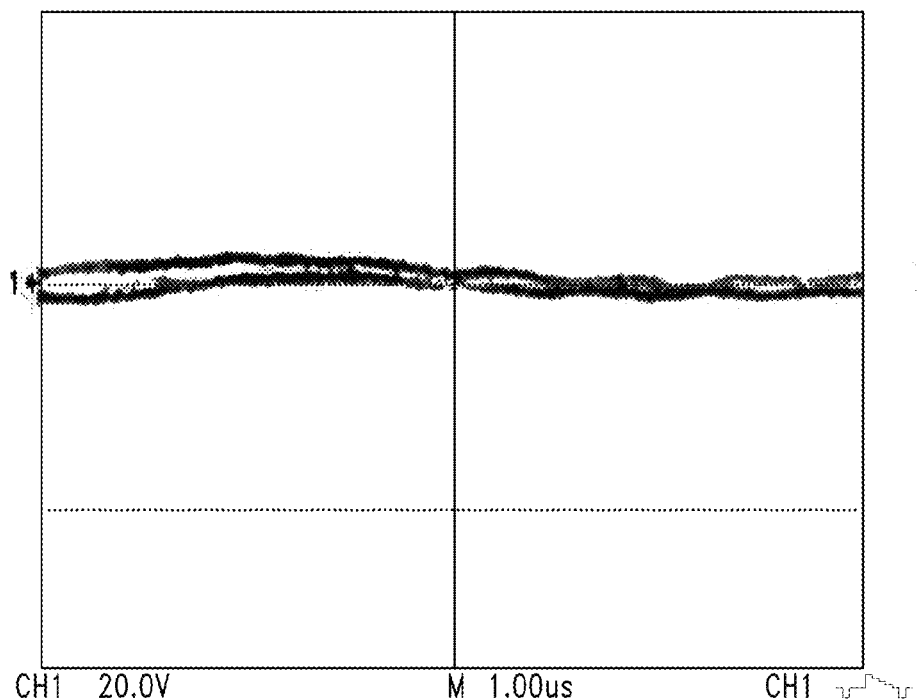

In FIG. 12A-12B, about 8-10 volt difference in the conductivity of the 200 volt pulse can be see at between the optically excited states (FIG. 12B) and unexcited states (FIG. 12A) with high ion saturation.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

Various changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A system for producing energized water comprising:
   a humidifying apparatus for generating a water molecule composition in a carrier gas, the water molecule composition being a water aerosol composition, water vapor, or a combination thereof, wherein the water aerosol composition includes water droplets suspended in the carrier gas, the water droplets being of micron-size, nano-size or a combination thereof;
   an excitation apparatus including one or more energy-emitting elements having peak emissions of electromagnetic energy of between about 500 nm to about 2900 nm for directly exciting the water aerosol composition with a sufficient amount of electromagnetic energy to provide energized water having an excited vibrational state;
   a control system operable to direct the electromagnetic energy to excite the water molecule composition, and
   a fluid management system adaptable for delivering the energized water into a passage way of a biological subject, wherein the fluid management system comprises an inhaler or a respirator.

2. The system of claim 1 wherein the humidifying apparatus converts pure water or an aqueous composition to the water aerosol composition.

3. The system of claim 2 wherein the aqueous composition comprises salts, minerals, vitamins, or one or more biologically active agents.

4. The system of claim 1 wherein the humidifying apparatus converts pure water or an aqueous composition to water vapor.

5. The system of claim 1 wherein the carrier gas is air, $O_2$, Ar, or $N_2$.

6. The system of claim 1 wherein the humidifying apparatus further comprises a temperature control element.

7. The system of claim 1 wherein the electromagnetic radiation is 520 nm, 640 nm, 1200 nm, 2900 nm, or a combination thereof.

8. The system of claim 1 wherein the one or more energy-emitting elements are a laser, a laser diode, a light emitting diode (LED), an arc flashlamp, or a continuous wave bulb.

9. The system of claim 1 wherein the energy-emitting elements provide two or more irradiation wavelengths.

10. The system of claim 1 wherein the energized water comprises excited state clathrate structures.

11. The system of claim 1 further comprising a fluid management system may be further communicatively coupled to the excitation apparatus and operable to direct a flow of the water molecule composition.

12. A system for producing energized water comprising:
    an excitation apparatus including one or more energy-emitting elements having peak emissions of electromagnetic energy of between about 500 nm to about 2900 nm for directly exciting a water aerosol composition with a sufficient amount of electromagnetic energy to provide energized water having an excited vibrational state, wherein the water molecule composition is a water aerosol composition, water vapor, or a combination thereof, and wherein the water aerosol composition includes water droplets suspended in the carrier gas, the water droplets being of micron-size, nano-size or a combination thereof;
    a control system operable to direct the electromagnetic energy to excite the water molecule composition, and
    a fluid management system adaptable for delivering the energized water into a passage way of a biological subject, wherein the fluid management system comprises an inhaler or a respirator.

13. The system of claim 12 wherein the electromagnetic radiation is 520 nm, 640 nm, 1200 nm, 2900 nm, or a combination thereof.

14. The system of claim 12 wherein the one or more energy-emitting elements are a laser, a laser diode, a light emitting diode (LED), an arc flashlamp, or a continuous wave bulb.

15. The system of claim 12 wherein the energy-emitting elements provide two or more irradiation wavelengths.

16. The system of claim 12 wherein the energized water comprises excited state clathrate structures.

17. The system of claim 12 further comprising a fluid management system may be communicatively coupled to the excitation apparatus and operable to direct a flow of the water molecule composition.

* * * * *